(12) United States Patent
Needleman et al.

(10) Patent No.: US 10,070,981 B2
(45) Date of Patent: Sep. 11, 2018

(54) LOCKING GASTRIC OBSTRUCTION DEVICE AND METHOD OF USE

(71) Applicant: BAROnova, Inc., Goleta, CA (US)

(72) Inventors: David Needleman, San Carlos, CA (US); Alex Roth, Redwood City, CA (US); Daniel R. Burnett, San Francisco, CA (US); Jimmy Van Westenberg, San Francisco, CA (US); Kobi Iki, San Carlos, CA (US)

(73) Assignee: BAROnova, Inc., San Carlos, CA (US)

( * ) Notice: Subject to any disclaimer, the term of this patent is extended or adjusted under 35 U.S.C. 154(b) by 85 days.

(21) Appl. No.: 14/849,450

(22) Filed: Sep. 9, 2015

(65) Prior Publication Data
US 2016/0206461 A1 Jul. 21, 2016

Related U.S. Application Data

(63) Continuation of application No. PCT/US2014/024475, filed on Mar. 12, 2014.

(60) Provisional application No. 61/791,433, filed on Mar. 15, 2013.

(51) Int. Cl.
*A61F 5/00* (2006.01)

(52) U.S. Cl.
CPC .......... *A61F 5/0079* (2013.01); *A61F 5/0089* (2013.01)

(58) Field of Classification Search
CPC ........ A61F 5/0079; A61F 5/0089; A61F 2/04; A61F 5/0076; A61F 5/0036; A61F 5/0003; A61B 17/08; A61B 17/02; A61B 17/22; A61B 17/083

USPC .......................................................... 606/191
See application file for complete search history.

(56) References Cited

U.S. PATENT DOCUMENTS

| 2,499,045 A | 2/1950 | Ray et al. |
| 3,154,077 A | 10/1964 | Cannon |
| 3,915,171 A | 10/1975 | Shermeta |
| 4,133,315 A | 1/1979 | Berman et al. |

(Continued)

FOREIGN PATENT DOCUMENTS

| DE | 4012642 | 10/1991 |
| JP | 2007-500538 | 1/2007 |

(Continued)

OTHER PUBLICATIONS

Lopasso, Fabio P. et al., "A Pilot Study to Evaluate the Safety, Tolerance, and Efficacy of a Novel Stationary Antral Balloon (SAB) for Obesity," Journal of Clinical Gastroenterology, vol. 42, No. 1, Jan. 2008, 48-53.

(Continued)

*Primary Examiner* — Katrina Stransky
(74) *Attorney, Agent, or Firm* — Levine Bagade Han LLP

(57) ABSTRACT

The present invention relates to a device for intermittently obstructing a bodily opening, such as a gastric opening, and includes a proximal member connected to a distal member by a tether. The proximal member is formable from an elongated and narrower configuration to a contracted or expanded but wider configuration. When employed in the stomach, the device may be arranged transluminally with the distal member disposed in the duodenum and the proximal member disposed against the pyloric valve, intermittently occluding the pyloric valve and preventing or delaying, the flow of gastric contents through the pyloric valve.

20 Claims, 18 Drawing Sheets

(56) References Cited

U.S. PATENT DOCUMENTS

| | | |
|---|---|---|
| 4,240,412 A | 12/1980 | James |
| 4,246,893 A | 1/1981 | Berson |
| 4,315,509 A | 2/1982 | Smit |
| 4,368,739 A | 1/1983 | Nelson |
| 4,416,267 A | 11/1983 | Garren et al. |
| 4,485,805 A | 12/1984 | Foster, Jr. |
| 4,517,979 A | 5/1985 | Pecenka |
| 4,598,699 A | 7/1986 | Garren et al. |
| 4,648,383 A | 3/1987 | Angelchik |
| 4,657,020 A | 4/1987 | Lifton |
| 4,694,827 A | 9/1987 | Weiner et al. |
| 4,735,214 A | 4/1988 | Berman |
| 4,762,128 A | 8/1988 | Rosenbluth |
| 4,836,204 A | 6/1989 | Landymore et al. |
| 4,878,905 A | 11/1989 | Blass |
| 4,925,446 A | 5/1990 | Garay et al. |
| 4,930,496 A | 6/1990 | Bosley |
| 4,946,440 A | 8/1990 | Hall |
| 5,011,488 A | 4/1991 | Ginsburg |
| 5,047,065 A | 9/1991 | Vogel et al. |
| 5,067,957 A | 11/1991 | Jervis |
| 5,108,420 A | 4/1992 | Marks |
| 5,129,915 A | 7/1992 | Carstens |
| 5,192,301 A | 3/1993 | Kamiya et al. |
| 5,234,454 A | 8/1993 | Bangs |
| 5,246,445 A | 9/1993 | Yachia et al. |
| 5,282,829 A | 2/1994 | Hermes |
| 5,306,300 A | 4/1994 | Berry |
| 5,312,343 A | 5/1994 | Krog et al. |
| 5,423,872 A | 6/1995 | Cigaina |
| 5,509,888 A | 4/1996 | Miller |
| 5,514,091 A | 5/1996 | Ycon |
| 5,514,178 A | 5/1996 | Torchio |
| 5,540,701 A | 7/1996 | Sharkey et al. |
| 5,545,210 A | 8/1996 | Hess et al. |
| 5,634,936 A | 6/1997 | Linden et al. |
| 5,674,192 A | 10/1997 | Sahatjian et al. |
| 5,676,688 A | 10/1997 | Jaker et al. |
| 5,707,355 A | 1/1998 | Zimmon |
| 5,750,585 A | 5/1998 | Park et al. |
| 5,752,971 A | 5/1998 | Rosenbluth et al. |
| 5,782,800 A | 7/1998 | Yoon |
| 5,820,584 A | 10/1998 | Crabb |
| 5,853,422 A | 12/1998 | Huebsch et al. |
| 5,947,991 A | 9/1999 | Cowan |
| 5,976,174 A | 11/1999 | Ruiz |
| 6,067,991 A | 5/2000 | Forsell |
| 6,102,928 A | 8/2000 | Bonutti |
| 6,112,703 A | 9/2000 | Handelsman |
| 6,117,159 A | 9/2000 | Huebsch et al. |
| 6,152,144 A | 11/2000 | Lesh et al. |
| 6,159,219 A | 12/2000 | Ren |
| 6,162,201 A | 12/2000 | Cohen |
| 6,183,520 B1 | 2/2001 | Pintauro et al. |
| 6,245,090 B1 | 6/2001 | Gilson et al. |
| 6,270,515 B1 | 8/2001 | Linden et al. |
| 6,371,974 B1 | 4/2002 | Brenneman et al. |
| 6,409,656 B1 | 6/2002 | Sangouard et al. |
| 6,454,785 B2 | 9/2002 | De Hoyos Garza |
| 6,488,962 B1 | 12/2002 | Berner et al. |
| 6,503,264 B1 | 1/2003 | Birk |
| 6,527,701 B1 | 3/2003 | Sayet et al. |
| 6,527,739 B1 | 3/2003 | Bigus et al. |
| 6,540,789 B1 | 4/2003 | Silverman et al. |
| 6,544,291 B2 | 4/2003 | Taylor |
| 6,558,400 B2 | 5/2003 | Deem et al. |
| 6,579,301 B1 | 6/2003 | Bales et al. |
| 6,600,953 B2 | 7/2003 | Flesler et al. |
| 6,652,578 B2 | 11/2003 | Bailey et al. |
| 6,675,809 B2 | 1/2004 | Stack et al. |
| 6,689,046 B2 | 2/2004 | Sayet et al. |
| 6,702,846 B2 | 3/2004 | Mikus |
| 6,740,121 B2 | 5/2004 | Geitz |
| 6,755,869 B2 | 6/2004 | Geitz |
| 6,802,868 B2 | 10/2004 | Silverman et al. |
| 6,860,895 B1 | 3/2005 | Akerfeldt et al. |
| 6,994,095 B2 | 2/2006 | Burnett |
| 7,011,621 B2 | 3/2006 | Sayet et al. |
| 7,037,344 B2 | 5/2006 | Kagan et al. |
| 7,054,690 B2 | 5/2006 | Imran et al. |
| 7,087,072 B2 | 8/2006 | Marino et al. |
| 7,120,498 B2 | 10/2006 | Imran et al. |
| 7,121,283 B2 | 10/2006 | Stack et al. |
| 7,122,058 B2 | 10/2006 | Levine et al. |
| 7,145,984 B2 | 12/2006 | Stack et al. |
| 7,160,312 B2 | 1/2007 | Saadat |
| 7,167,750 B2 | 1/2007 | Knudson et al. |
| 7,186,251 B2 | 3/2007 | Malecki et al. |
| 7,320,696 B2 | 1/2008 | Gazi et al. |
| 7,588,584 B2 | 9/2009 | Fogarty et al. |
| 7,803,195 B2 | 9/2010 | Levy et al. |
| 7,842,053 B2 | 11/2010 | Chanduszko et al. |
| 8,048,169 B2 | 11/2011 | Burnett et al. |
| 8,257,389 B2 | 9/2012 | Chanduszko et al. |
| 2002/0013601 A1 | 1/2002 | Nobles et al. |
| 2002/0038100 A1 | 3/2002 | Okada |
| 2002/0091395 A1 | 7/2002 | Gabbay |
| 2002/0165589 A1 | 11/2002 | Imran et al. |
| 2002/0188354 A1 | 12/2002 | Peghini |
| 2002/0198470 A1 | 12/2002 | Imran et al. |
| 2002/0198479 A1 | 12/2002 | Talish |
| 2003/0023150 A1 | 1/2003 | Yokoi et al. |
| 2003/0040804 A1 | 2/2003 | Stack et al. |
| 2003/0078611 A1 | 4/2003 | Hashiba et al. |
| 2003/0093117 A1 | 5/2003 | Saadat |
| 2003/0109931 A1 | 6/2003 | Geitz |
| 2003/0109935 A1 | 6/2003 | Geitz |
| 2003/0120328 A1 | 6/2003 | Jenkins et al. |
| 2003/0144708 A1 | 7/2003 | Starkebaum |
| 2003/0152601 A1 | 8/2003 | Kanayama |
| 2003/0153806 A1 | 8/2003 | Miller |
| 2003/0158601 A1 | 8/2003 | Silverman et al. |
| 2004/0034408 A1 | 2/2004 | Majercack |
| 2004/0059368 A1 | 3/2004 | Maryanka |
| 2004/0107004 A1 | 6/2004 | Levine et al. |
| 2004/0117031 A1 | 6/2004 | Stack et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0213825 A1 | 10/2004 | Levy |
| 2004/0230222 A1 | 11/2004 | van der Burg et al. |
| 2004/0236357 A1 | 11/2004 | Kraemer et al. |
| 2004/0267378 A1 | 12/2004 | Gazi et al. |
| 2005/0033331 A1 | 2/2005 | Burnett et al. |
| 2005/0033332 A1 | 2/2005 | Burnett |
| 2005/0038460 A1 | 2/2005 | Jayaraman |
| 2005/0038470 A1 | 2/2005 | Van Der Burg et al. |
| 2005/0055039 A1 | 3/2005 | Burnett et al. |
| 2005/0064009 A1 | 3/2005 | Bates |
| 2005/0090873 A1 | 4/2005 | Imran et al. |
| 2005/0096673 A1 | 5/2005 | Stack et al. |
| 2005/0149142 A1 | 7/2005 | Starkebaum |
| 2005/0192627 A1 | 9/2005 | Whisenant et al. |
| 2005/0192629 A1 | 9/2005 | Saadat et al. |
| 2005/0251154 A1 | 11/2005 | Chanduszko et al. |
| 2005/0273060 A1 | 12/2005 | Levy et al. |
| 2005/0288786 A1 | 12/2005 | Chanduszko |
| 2006/0020278 A1 | 1/2006 | Burnett et al. |
| 2006/0178691 A1 | 8/2006 | Binmoeller |
| 2006/0217763 A1 | 9/2006 | Abbott et al. |
| 2006/0259074 A1 | 11/2006 | Kelleher et al. |
| 2006/0282107 A1 | 12/2006 | Hashiba et al. |
| 2006/0293742 A1 | 12/2006 | Dann et al. |
| 2007/0016262 A1 | 1/2007 | Gross et al. |
| 2007/0056591 A1 | 3/2007 | McSwain |
| 2007/0083224 A1 | 4/2007 | Hively |
| 2007/0135831 A1 | 6/2007 | Burnett et al. |
| 2007/0178160 A1 | 8/2007 | Burnett |
| 2007/0198082 A1 | 8/2007 | Kapadia et al. |
| 2007/0239284 A1 | 10/2007 | Skerven et al. |
| 2007/0250132 A1 | 10/2007 | Burnett |
| 2009/0018757 A1 | 5/2009 | Burnett et al. |
| 2009/0118757 A1 | 5/2009 | Burnett et al. |
| 2009/0118758 A1 | 5/2009 | Burnett et al. |

(56) References Cited

U.S. PATENT DOCUMENTS

| | | |
|---|---|---|
| 2009/0177288 A1 | 7/2009 | Wallsten |
| 2009/0182357 A1* | 7/2009 | Burnett ............ A61B 17/12099 606/157 |
| 2009/0182358 A1 | 7/2009 | Burnett et al. |
| 2009/0187200 A1 | 7/2009 | Burnett et al. |
| 2009/0187201 A1 | 7/2009 | Burnett et al. |
| 2009/0198210 A1 | 8/2009 | Burnett et al. |
| 2009/0216262 A1 | 8/2009 | Burnett et al. |
| 2009/0299486 A1 | 12/2009 | Shohat et al. |

FOREIGN PATENT DOCUMENTS

| | | |
|---|---|---|
| JP | 2010-537790 | 12/2010 |
| WO | WO 1988/00027 | 1/1988 |
| WO | WO 1990/00369 | 1/1990 |
| WO | WO 2000/048672 | 8/2000 |
| WO | WO 2002/091961 | 11/2002 |
| WO | WO 2003/017882 | 3/2003 |
| WO | WO 2005/009288 | 2/2005 |
| WO | WO 2005/104989 | 10/2005 |
| WO | WO 2006/020370 | 2/2006 |
| WO | WO 2006/135857 | 12/2006 |
| WO | WO 2007/027812 | 3/2007 |
| WO | WO 2007/092390 | 8/2007 |
| WO | WO 2007/092501 | 8/2007 |
| WO | WO 2009/033049 | 3/2009 |

OTHER PUBLICATIONS

U.S. Appl. No. 10/671,191, filed Sep. 24, 2003.
U.S. Appl. No. 10/833,950, filed Apr. 27, 2004.
U.S. Appl. No. 10/915,716, filed Aug. 9, 2004.
U.S. Appl. No. 11/215,430, filed Aug. 29, 2005.
U.S. Appl. No. 11/602,620, filed Nov. 20, 2006.
U.S. Appl. No. 11/702,840, filed Feb. 5, 2007.
U.S. Appl. No. 11/702,888, filed Feb. 5, 2007.
U.S. Appl. No. 12/351,705, filed Jan. 9, 2009.
U.S. Appl. No. 12/351,686, filed Jan. 9, 2009.
U.S. Appl. No. 12/351,665, filed Jan. 9, 2009.
U.S. Appl. No. 12/351,644, filed Jan. 9, 2009.
U.S. Appl. No. 12/434,594, filed May 1, 2009.
U.S. Appl. No. 14/618,868, filed Feb. 10, 2015.
U.S. Appl. No. 12/205,403, filed Sep. 5, 2008.
U.S. Appl. No. 12/352,497, filed Jan. 12, 2009.
U.S. Appl. No. 12/352,508, filed Jan. 12, 2009.
U.S. Appl. No. 14/495,371, filed Sep. 24, 2014.

* cited by examiner

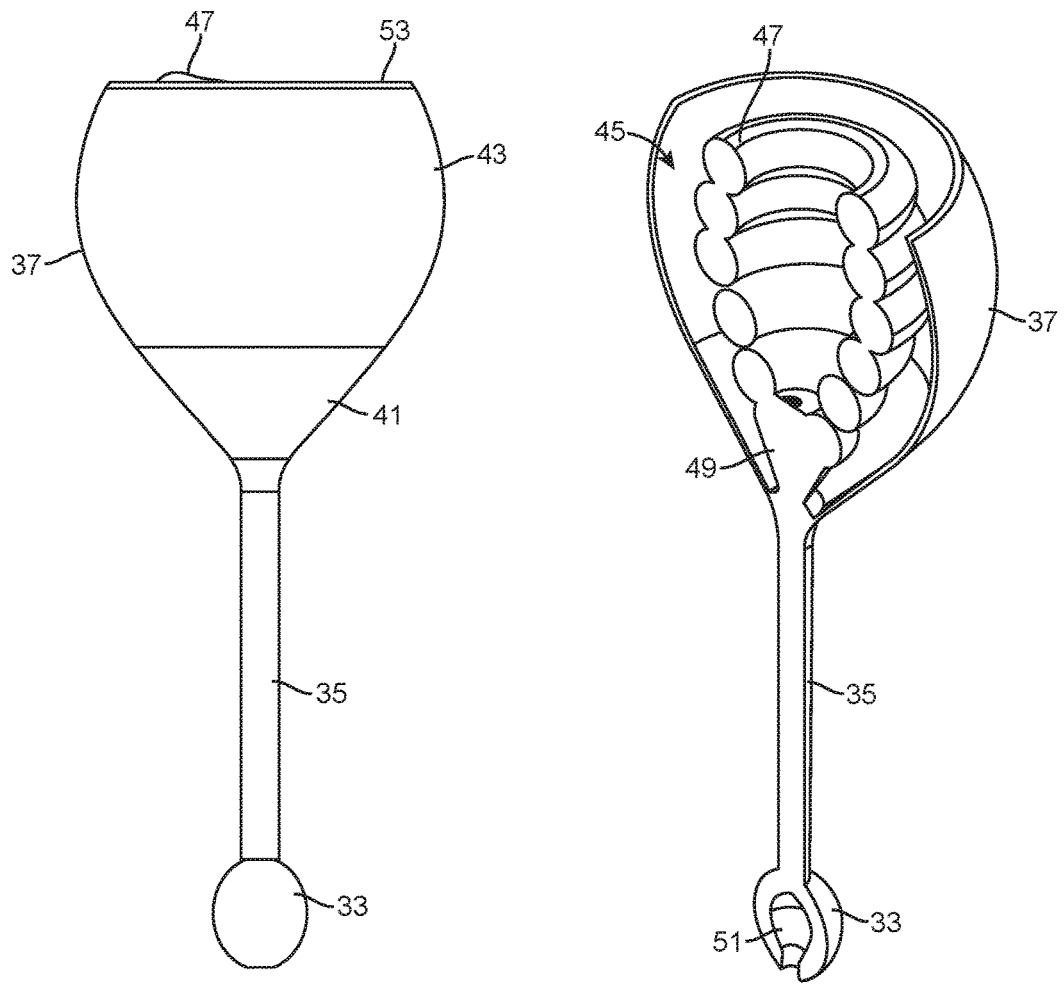

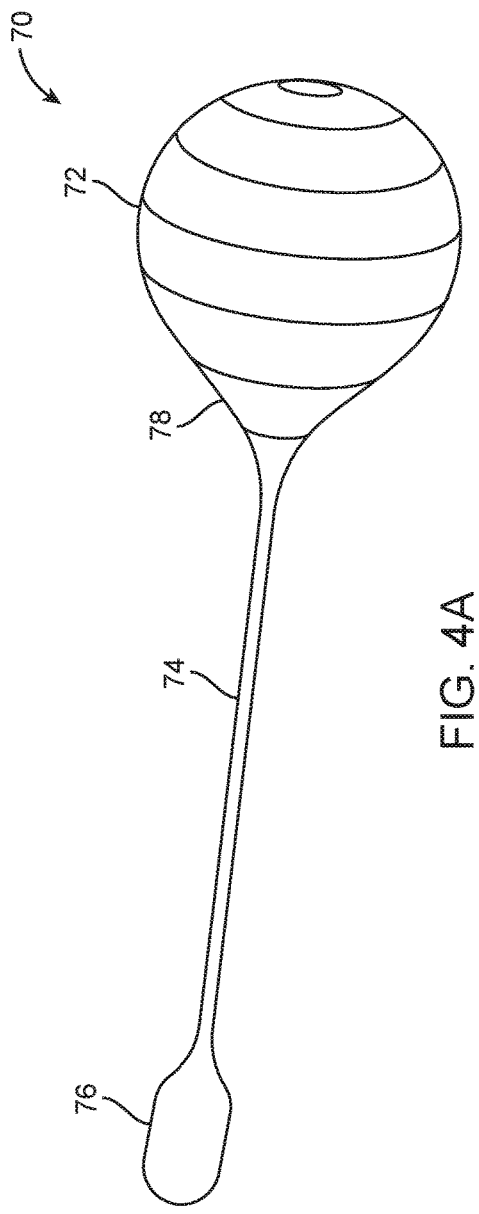
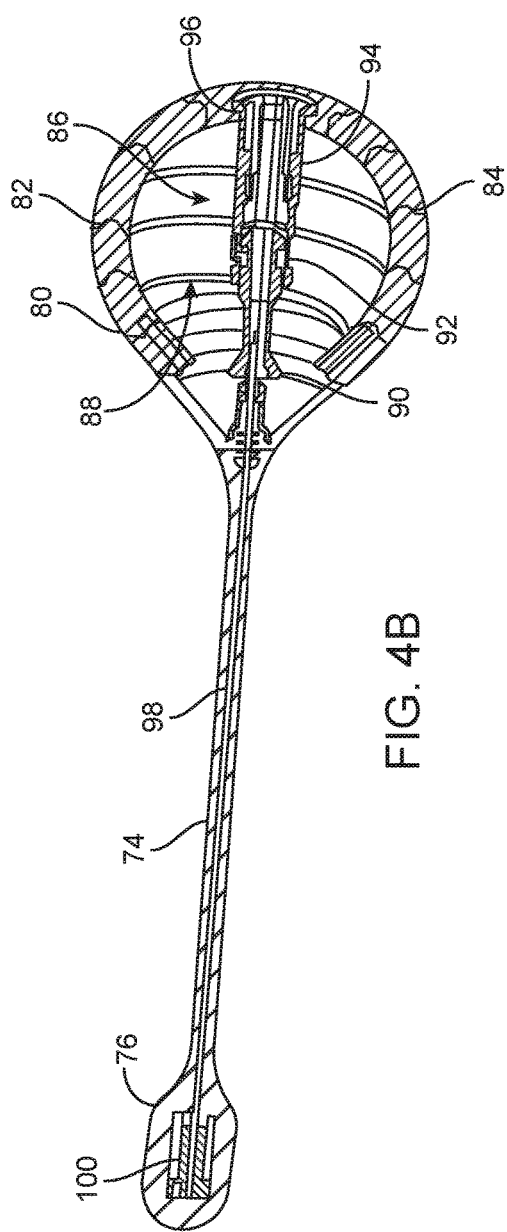
FIG. 4A
FIG. 4B

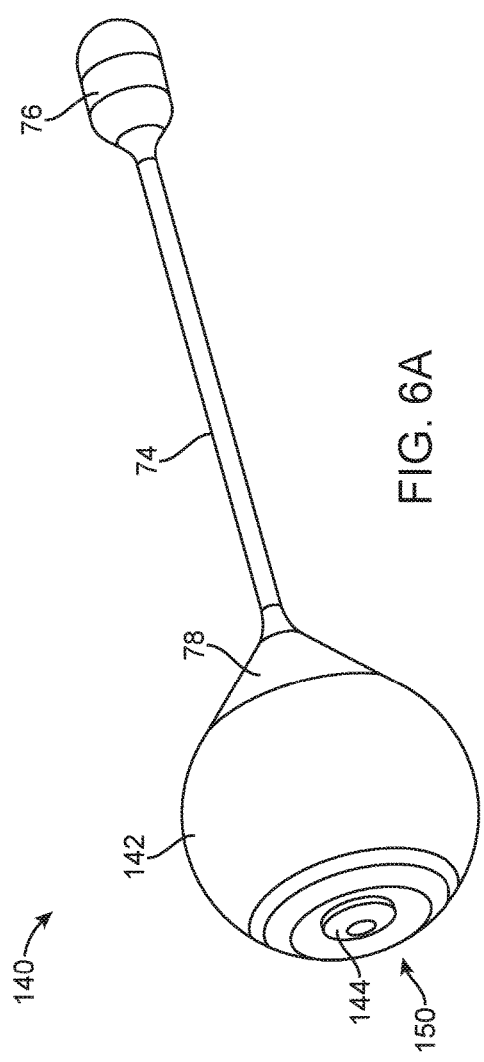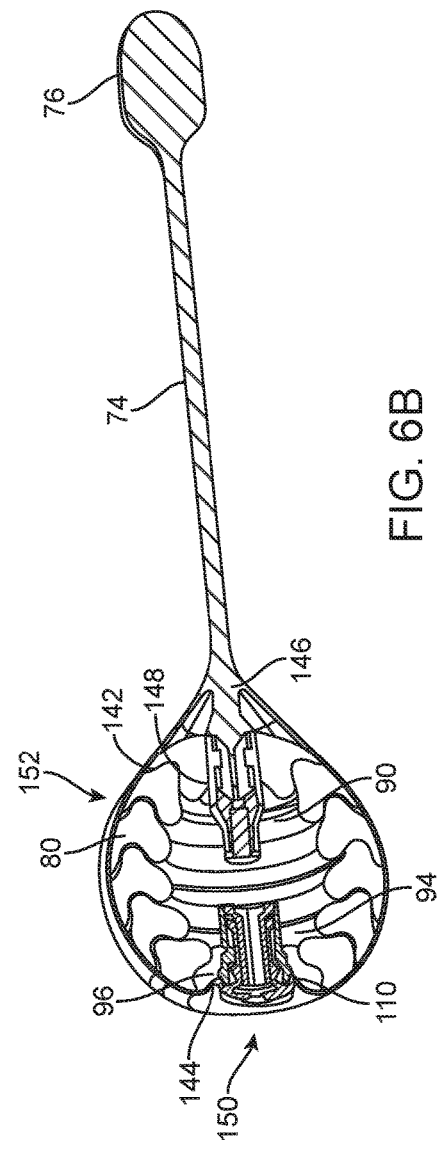

LOCKING GASTRIC OBSTRUCTION DEVICE AND METHOD OF USE

CROSS-REFERENCE TO RELATED APPLICATIONS

This application is a continuation of International Application No. PCT/US2014/024475 filed Mar. 12, 2014, which claims the benefit of priority to U.S. Provisional Application No. 61/791,433 filed Mar. 15, 2013, which is incorporated herein by reference in its entirety.

FIELD OF THE INVENTION

The present invention relates to a gastro-intestinal device for treating obesity and other medical conditions. More particularly, the present invention relates to a device that is positioned transluminally in a patient's gastro-intestinal tract to intermittently obstruct or reduce the flow of gastric contents.

BACKGROUND OF THE INVENTION

Obesity is a condition of epidemic proportions in the United States. Recent government studies have indicated that up to 40% of Americans are obese and that, among those, almost 20% are morbidly obese. Obesity is not the problem in and of itself, but is the source of multiple pathological conditions, including cardiovascular disease, heart disease, stroke, diabetes, and obstructive sleep apnea. Recent studies have indicated that obesity can reduce a person's lifespan by an average of three years in adults and twenty years in children.

Many attempts have been made in the prior art to provide medications, devices, and surgical procedures for the treatment of obesity, all of which either have serious side effects or are basically ineffective. For example, various diets, supplements and pharmaceuticals have been developed, and marketed, but none have shown any significant benefits to date in the treatment of obesity with the exception of some pharmaceuticals, which have unfortunately been found to cause a number of serious, life-threatening medical conditions. To date, there are no commercially available supplements or drugs that have been proven to be effective in promoting significant weight loss and at the same time that are free from serious collateral side effects.

Recognizing that no cure has been developed to date that is both effective and safe, the medical industry has introduced more extreme procedures, an example of which is the Roux-En-Y gastric, bypass. This extensive and invasive surgery is highly effective but is also potentially lethal, with a 1-2% mortality rate, a six month recovery period, and a cost of tens of thousands of dollars, yet it is becoming increasingly popular because other available treatments do not produce the desired results. Gastric reduction, or simply removing a large segment of the stomach, another procedure that is similar to gastric bypass and that, like gastric bypass, has also been associated with potentially lethal complications. Data from recent studies have indicated that even in the lowest risk groups, obesity surgery causes an average one-year mortality rate of nearly 5%.

In another attempt to treat obesity, devices have also been developed in the prior art that are aimed at providing a sense of fullness to a patient, so to cause the patient to reduce food intake. Such devices may be configured as stents that support the stomach or the pyloric valve to or that may be configured as permanent occluders. Unfortunately, these devices are implanted in the patient on an essentially permanent basis and typically include complex mechanical or electrical features that may stop working properly over time or that may require maintenance from time to time. Examples of such devices in the prior art can be found m U.S. Pat. Nos. 5,509,888; 6,067,991; 6,527,701; 6,689,046; 7,011,621; 7,037,344; 7,120,498; 7,122,058 and 7,167,750, and in U.S. Patent Application Publications Nos. 2004/0172142; 2005/0273060; 2007/0016262; 2007/0027548; and 2007/0081224.

Evidence has been developed showing that benefits can be derived from reducing gastroduodenal flow. In unpublished, but recently presented data at the American Society for Bariatric Surgery conference of June 2003, stimulation of the gastric vagus nerve with subsequent reduction in gastric motility resulted in a loss of over 20% of excess weight over a nine month period. Furthermore, there is data suggesting that gastric vagotomy is also effective in the treatment of obesity trough a similar mechanism. Unfortunately, these therapies require highly invasive, sometimes irreversible, surgical procedures, making undesirable for a large segment of the obese population.

BRIEF SUMMARY OF THE INVENTION

It is an object of the present invention to provide a device for the treatment of obesity and related conditions that intermittently obstructs a transluminal passage, such as a gastric opening.

It is also an object of the present invention to provide a device for the treatment of obesity and related conditions that is well tolerated by the stomach and in general, by the gastro-intestinal tact.

It is a further object of the present invention to provide a device for the treatment of obesity and related conditions that can be implanted and removed with medical procedures that are safe and relatively simple to perform.

Briefly, the device of the present invention operates as a transluminal device that obstructs the pylorus or other organ on an intermittent basis and that causes a reduced flow of gastric contents into the intestinal tract. The device of the present invention may just occupy space in the stomach and occlude the pyloric valve from time to time, or also may partially obstruct the duodenum or the small intestine, reducing overall gastrointestinal transit. The intermittent blockage of the gastrointestinal tract results in weight loss and also in an increased or sustained feeling of fullness by the patient.

The device of the present invention can be placed and removed with simple endoscopic procedures and is completely reversible. In particular, the device of the present invention can be inserted and removed orally, nasally or transcutaneously and, in certain embodiments, can be triggered externally or can be caused to expand or can self-expand once in the gastrointestinal space.

In one embodiment, a device according to the present invention includes a proximal member oriented in the direction of the stomach after implantation and a distal member oriented in the direction of the duodenum after implantation that are connected by a tether.

The proximal member is composed of a first occluding member surrounded by an apron member. The first occluding member is formable from an elongated, narrower configuration to a contracted, wider configuration, while the apron member has an essentially cylindrical portion that surrounds the first occluding member and an essentially conical portion that connects the apron member to the tether, providing the apron member with a funnel-like shape. In one embodiment, the cylindrical portion is spaced from the first occluding member by an interstice, and the cylindrical and conical portions may have different wall thickness.

The first occluding member may be formable from the narrower configuration to the wider configuration by injecting a substance within the first occluding member, or may have a solid structure that can be compressed to assume an expanded shape, in order to transition form the elongated configuration to the wider configuration.

In one embodiment, the elongated configuration exhibits a helical contour with a plurality of turns, and the wider configuration is formed from the helical configuration by nesting the turns one adjacent to the other to provide a bulbous body. The wider configuration is then locked in place by engaging a connecting member at the proximal end of the first occluding member with a mating cavity at the distal end of the first occluding member. This may be achieved by having a clinician pull on a string coupled to the connecting member in the direction of the mating cavity.

In one embodiment, such coupling, string extends outside of the device along its entire length and then enters a lumen running from the first occluding member to the second occluding members through the tether. When entering the first occluding member, the string is looped through the connecting member and is removable from the device after the connecting, member has engaged the matching cavity. The proximal end of the first occluding member may be reinforced to increase its resistance to tear during the compression of the first occluding member by including a reinforcing material in at least part of the structure of the proximal end.

The transformation process from the elongated configuration to the wider configuration is reversible so that the device can be implanted in the stomach in the elongated configuration, reside in the stomach and/or gastro-intestinal tract in the wider configuration, and be removed from the stomach through the esophagus in the elongated configuration. In one embodiment, the wider configuration reverses to the elongated configuration by severing the connecting member from the proximal end, for example, by having a clinician cut a string coupling the connecting member to the proximal end or to a release member in the proximal end.

A device according to the present material is manufactured from a material that is biocompatible, that is able to withstand the gastrointestinal environment, and that prevents or anyways minimizes abrasion of the walls of the stomach and duodenum, particularly of the pyloric valve, in one embodiment, the device is manufactured from a resilient plastic material, for example, from a silicone material, and the apron member may be constructed to be flexible enough to reverse from a position surrounding a portion of the tether to a position surrounding the first occluding member, in order to facilitate insertion in the stomach according to one method of use.

The second occluding member also may have a bulbous shape, like a pod, and include an insert having a heavier weight than the remainder of the second occluding, member, so to facilitate disposition and retention in the duodenum.

The device of the present invention is suited not only for the treatment of obesity, but also for treating other ailments, such as improper glucose tolerance in a diabetic or prediabetic subject and the progression of diabetes itself by inhibiting fasting insulin secretion or glucose-stimulated insulin secretion. The resent device is also suited for treating other ailments deriving from obesity, including hyperphagia, dyslipidemia, Prader Willi syndrome, Froelich's syndrome, Cohen syndrome, Summit syndrome, Alstrom syndrome, Borjesen syndrome, Bardet-Biedl syndrome, or hyperlipoproteinemia, types I, II, III, and IV.

The device of the present invention may also include sensors or transmitters to provide feedback and other data to an intra-corporeal or extra-corporeal processor, or may carry one or more compounds stored in a reservoir within the device or coated on the device. In one embodiment, insulin is released into the gastro-intestinal tract by disposing an insulin reservoir in the distal member of the device. Such a release of insulin may be controlled by the size of the orifice between the reservoir and the outer environment, or by a time-controlled actuator, or by an actuator controlled by one or more sensors, for example in response to detection of sugar in the gastro-intestinal tract.

Other embodiments of the present invention, methods of use of a device manufactured according to the present invention, and methods of treatment of a variety of ailments using, the device of the present invention are discussed in detail in the following sections. Additionally, alternative devices and their methods of use which may be used with the features described herein in various combinations are further described in detail in U.S. patent application Ser. No. 12/205,403 filed Sep. 5, 2008 (US Pub. 2009/0198210); U.S. patent application Ser. No. 12/352,497 filed Jan. 12, 2009 (US Pub. 2009/0182357); and U.S. patent application Ser. No. 12/352,508 filed Jan. 12, 2009 (US Pub. 2009/0182358), each of which is incorporated herein by reference in its entirety for any purpose.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

FIGS. 2D-2E illustrate respective side and cross-sectional perspective views of the embodiment of FIGS. 2A-2C.

FIGS. 4A and 4B show perspective views of a helical assembly having, a proximal member reconfigured from its elongated configuration into its enlarged, coiled and nested configuration.

FIGS. 6A and 6B show perspective and cross-sectional perspective views of a covered obstructing assembly.

DETAILED DESCRIPTION OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1A:
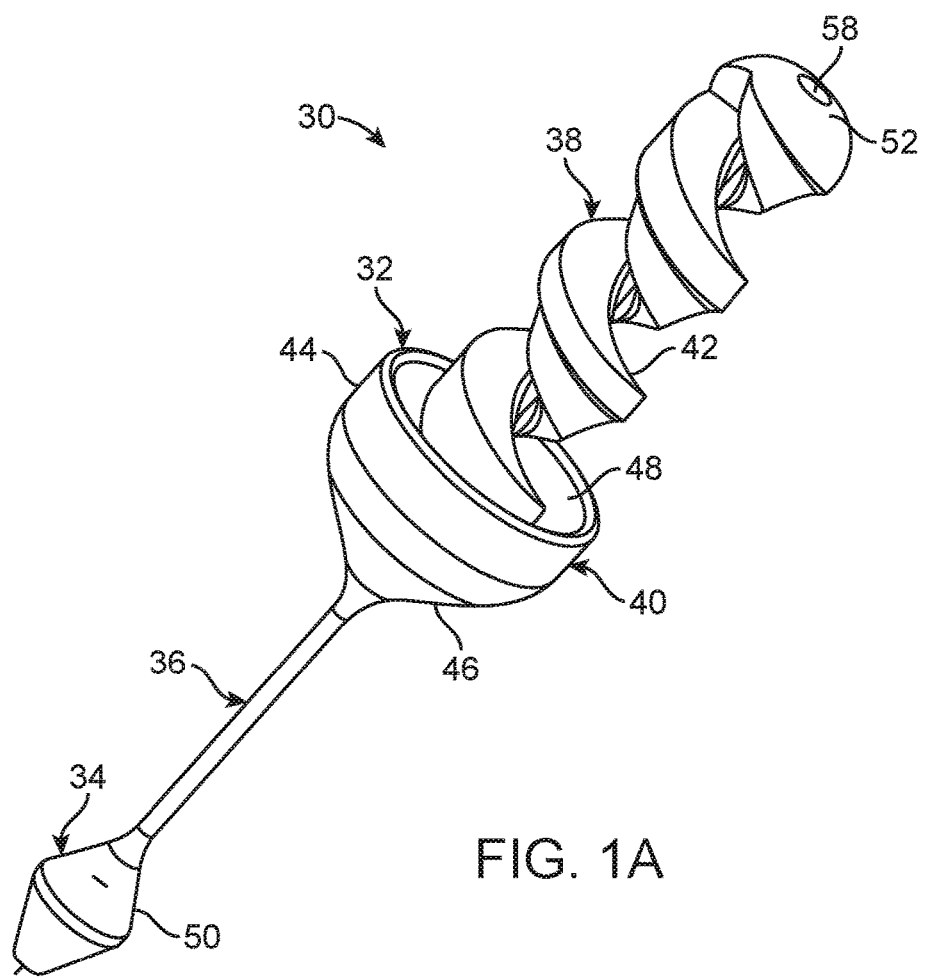
FIG. 1A illustrates a perspective view of a first embodiment of the invention in the elongated, narrower configuration.

FIG. 1A depicts a first embodiment of the invention, which is configured for insertion into a patient's organ, typically the stomach. Device 30 includes a proximal member 32 and a distal member 34, which are connected one to the other by a tether 36. The relative sizes of proximal member 32 and of distal member 24 are such that, after insertion into the stomach of a patient, the natural contractions of the stomach and, in general, the movements of the patient induce distal member 34 to enter the pyloric part of the gastro-intestinal tract and the duodenum, while proximal member 32 is retained in the stomach and cannot move beyond the pyloric valve because its diameter is larger than the pyloric valve opening.

Figure 1B:
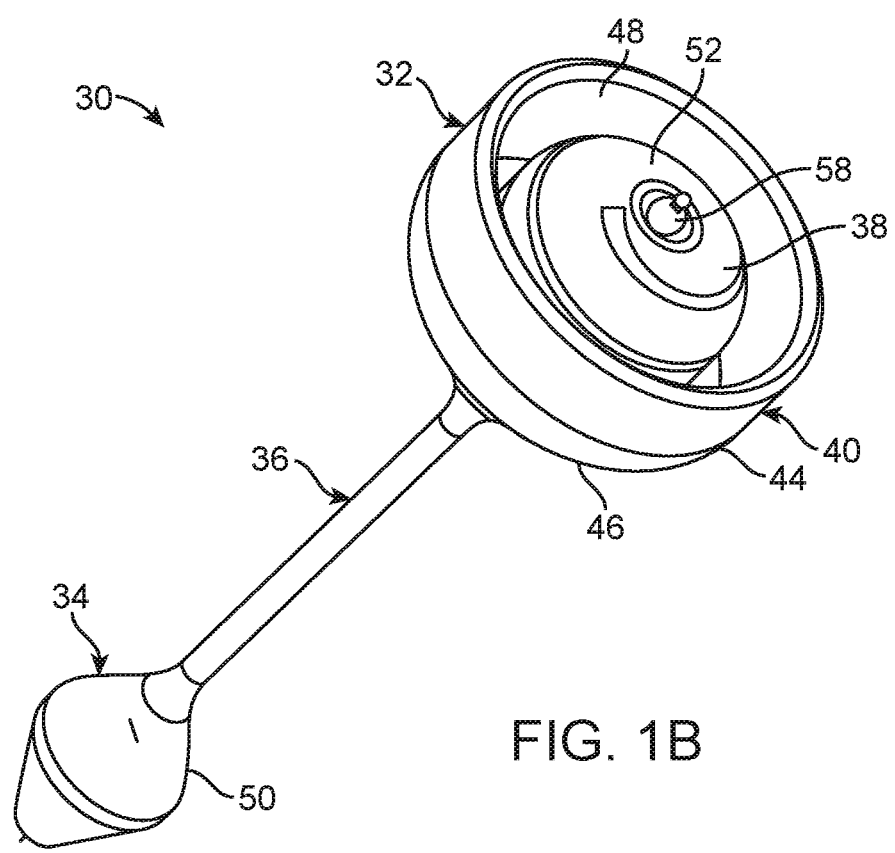
FIG. 1B illustrates a perspective view of the embodiment of FIG. 1A in the contracted, wider configuration.

More particularly, proximal member 32 includes a first occluding member 38, disposed in a central position within an apron member 40. First occluding, member 38 may be formed from an elongated, narrower configuration as shown in FIG. 1A to a contracted, wider configuration as shown in FIG. 1B. In the embodiment illustrated in FIG. 1A, first occluding member 38 has a helical design with a plurality of turns 42, which are configured to nest one adjacent to the other to assume the compact, bulbous shape illustrated in FIG. 1B.

Apron member 40 wraps around first occluding member 38, providing proximal member 32 with a enlarged diameter and preventing the passage of proximal member 32 through the pyloric valve. In one variant of the present embodiment, apron member 40 includes an essentially cylindrical proximal portion 44 connected to an essentially conical distal portion 46 that extends from tether 36 to proximal portion 44. This configuration of apron member 40 is designed to provide an intermittent plugging effect on the pyloric valve and to avoid or anyways minimize abrasive contact with the wall of the pyloric valve during such plugging effect, so to prevent or minimize patient discomfort and irritations or even lacerations to the mucosa of the stomach and, in general, to the gastro-intestinal tract.

Distal portion 46 may have a smaller wall thickness than proximal portion 44, both providing a gentler, suppler contact with the pyloric valve, and also facilitating the reversal of apron member 44 during insertion into a patient's stomach from a position substantially aligned with tether 36 to the position that wraps around first occluding member 38, as explained in greater detail below.

In different variants of the present embodiment, apron member 40 may extend proximally for various lengths, surrounding first occluding member 38 partially or completely. Further, in different variants of the present embodiment, apron member 40 may be spaced from first occluding member 38 at various distances to create an interstice 48 of different amplitudes between first occluding member 38 and apron member 40.

Second occluding member 34 may exhibit a variety of contours and in general, is shaped to facilitate its transition out of the stomach and into the duodenum, and to avoid or minimize abrasive contact with the walls of the stomach and of the pylorus. In one embodiment, second occluding member 34 has a bulbous shape, essentially formed by two rounded, frusto-conical portions 50 connected at their wider bases.

Device 30 may be manufactured from a variety of materials, for example, from a resilient plastic such as a silicone or urethane plastic, which may be reinforced in selected portions. In general, the selected material should be biocompatible, resistant to the stomach environment, for example to stomach acids, and soft to the contact with the stomach and duodenal walls. The desired material should also provide device 30 with the desired shape while retaining sufficient flexibility for the insertion process in the stomach, for later reverting to the desired position within the gastro-intestinal tract, and for adapting to the various movements of the stomach and, in general, of the body of the patient.

Inserts may be integrally included within the body of device 30 to increase certain mechanical properties in certain areas. For example, an insert such as a metallic cylinder) may be embedded within second occluding member 34 to increase weight and to facilitate retention by gravity within the pylorus. Another insert (such as a fabric piece) may also be embedded in proximal end 52 of first occluding member 38, increasing resistance to tear when proximal end 52 is pulled outwards to extend first occluding member to the configuration of FIG. 1, or inwards to stabilize first occluding member in its contracted, wider configuration, as explained in greater detail below.

Figure 1C:
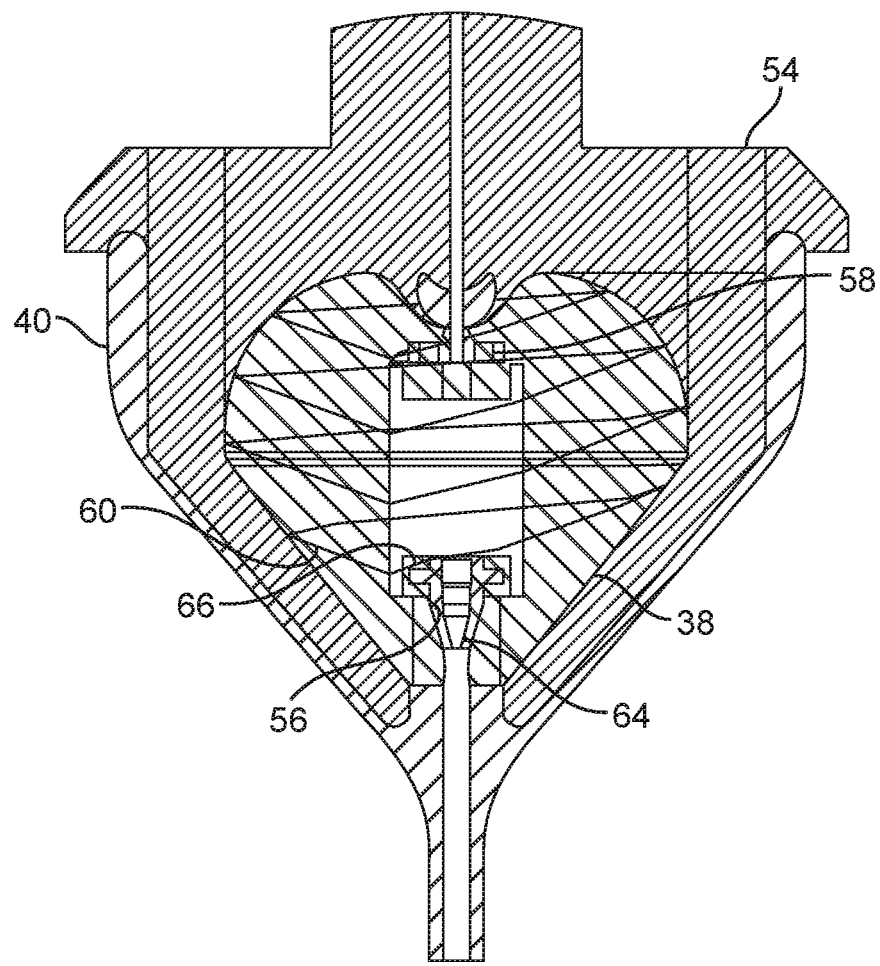
FIGS. 1C-1E illustrate respectively a cross-sectional view of the proximal member of the embodiment of FIG. 1B, to which a protective cap has been added (FIG. 1C) a side view of the embodiment of FIG. 1B with the protective cap (FIG. 1D); and a cross-sectional view of the embodiment of FIG. 1D (FIG. 1E).
Figures 1D, 1E:
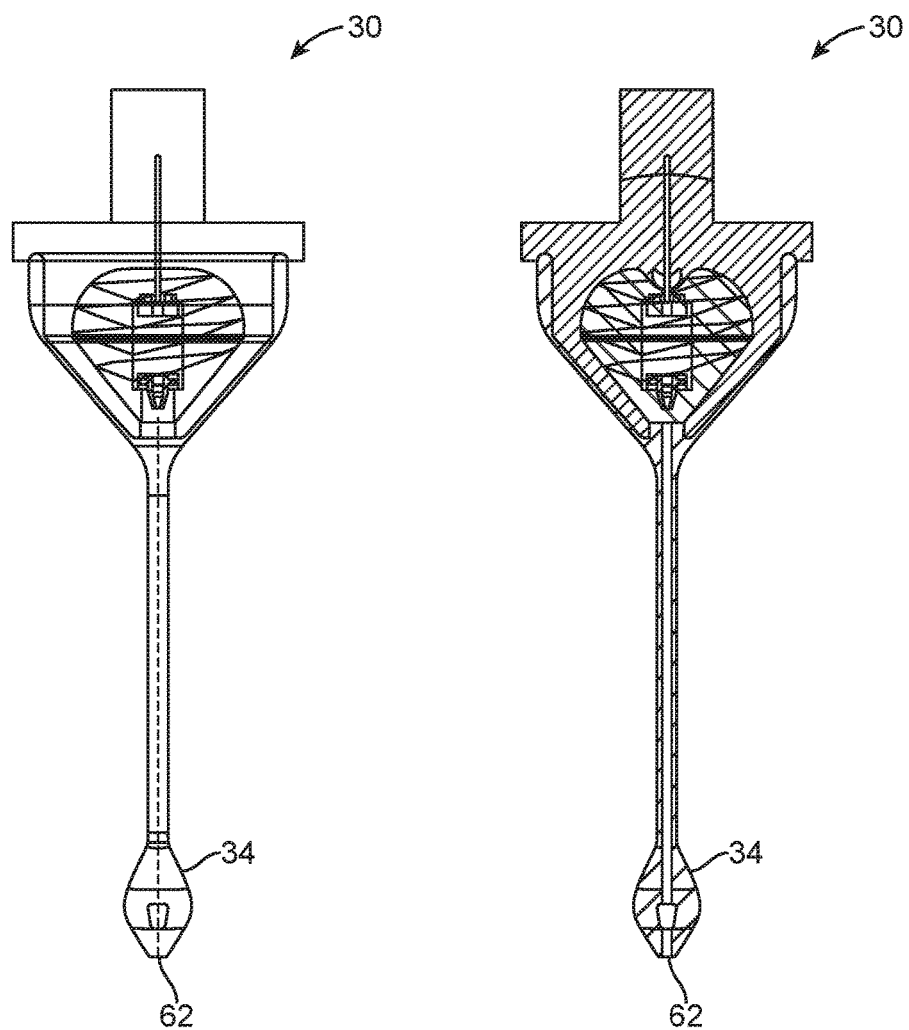
Figure 1F:
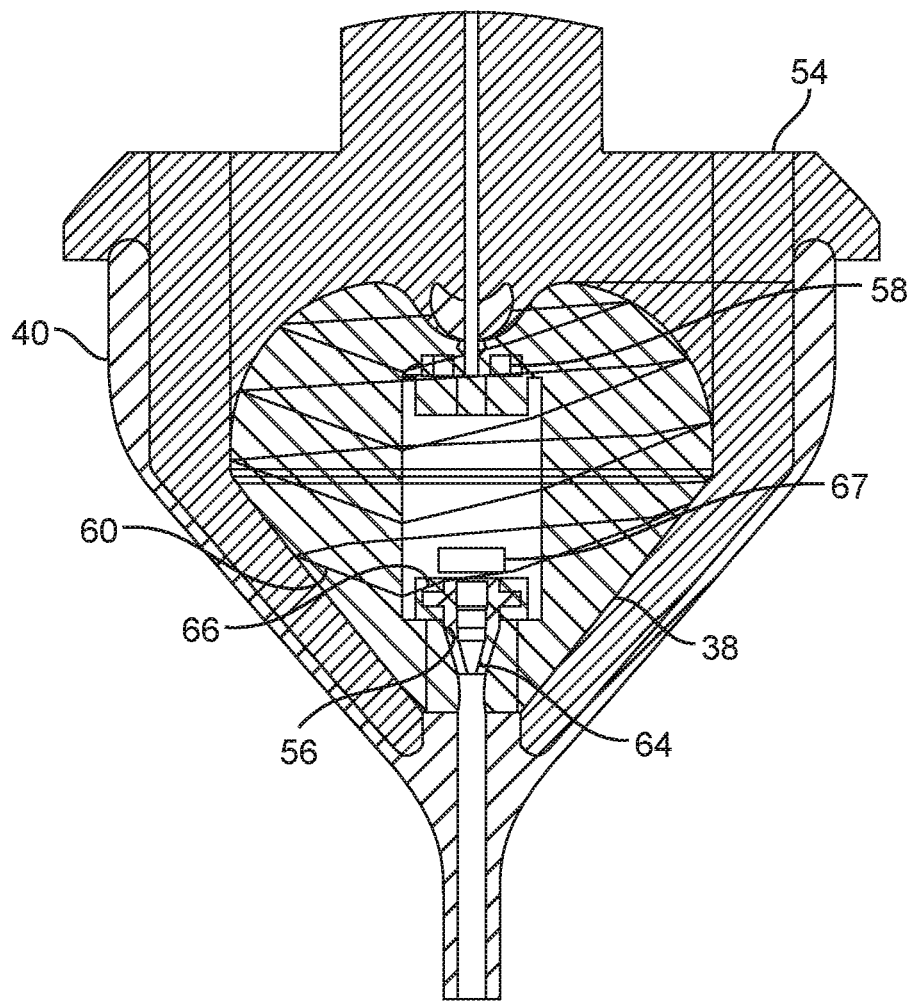
FIG. 1F illustrates a cross-sectional side view of one example of a device having a sensor incorporated within for confirming or detecting whether the occluding member has been locked into its deployment configuration.

The insertion of device 30 in a patient's stomach will now be described with reference to FIG. 1C. It should be noted that FIG. 1C illustrates, among other things, one variant of the embodiment of FIGS. 1A and 1B, in which a stabilizing cap 54 is added to maintain first occluding member 38 in the contracted, wider configuration, and also to increase bulk and to prevent the introduction of food or other gastric products within interstice 48.

In one method of use, device 30 is introduced in a patient's stomach in the elongated, narrower configuration of FIG. 1A, with apron member 40 oriented in the opposite direction to that shown in FIG. 1A, that is, to cover tether 36 while the free end of distal portion 46 is oriented proximally, in the direction of second occluding member 34. When in this configuration, device 30 is disposed within a tube (not shown) and is caused to exit the tube with proximal end 52 first, followed by the rest of the device. When device 30 has partially exited the tube (or alternatively, the tube has been retracted from device 30) so to leave apron member 40 outside of the tube, device 30 is pulled inside the tube, but because apron member 40 surrounds and wraps around the end of the tube, such a pulling of device 30 inwards into the tube, causing apron member 40 to flip over and change orientation, so to wrap around first occluding member 38. After such a flipping around of apron member 40 has been achieved, device 30 is completely ejected from the tube and becomes disposed in the stomach. Alternatively, device 30 may be introduced in a patient's stomach with apron member 40 already oriented proximally, making unnecessary the previously described flipping operation.

While the configuration of first occluding member 38 makes it recoil and assume the contracted configuration, similar to that shown in FIG. 1B, the fully contracted, wider configuration of first occluding member 38 is achieved and maintained as follows. A connecting member 56 is coupled (for example, by a first string) to a release member 58. A second string 60 is looped around device 30, miming outside and along, device 30 starting from a first free end, and then extending within connecting member 56 through lumen 66, and then (within a lumen or a tube) within turns 42, successively entering a lumen 62 in tether 36 and second occluding member 34 (see also FIGS. 1D and 1E), and eventually exiting device 30 with a second free end.

After device 30 has been introduced in the stomach, a clinician can hold both ends of second string 60 and, by pulling on second string 60 while device 30 is constrained within the stomach, the clinician causes connecting member 56 to travel in the direction of mating cavity 64, shaped so to constrain connecting member 56 (for example, by interference fit) and to prevent connecting member 56 from being released. Therefore, first occluding member 38 is locked into its contracted, wider condition on a permanent basis.

After device 30 has been shaped as described, second string 60 is removed by pulling on one free end and by having second string 60 slide through the lumens within device 30, eventually exiting device 30 entirely. Device 30 is now free to move freely within the stomach, and the natural contractions of the stomach, in addition to any other movements of the patient's body, cause distal member 34 to move into the pylorus, while the size of proximal member 32 prevents it from moving into the pylorus and forces it to reside in the stomach. Therefore, distal member 34 will eventually be disposed in the pylorus, and any inserts of a heavier weight will facilitate retention of distal member 34 in the pylorus, while proximal member 32 will act as an intermittent plug against the pyloric valve, because stomach contractions and other body movements will cause proximal member 32 to move towards and away from the pyloric valve, acting as an intermittent plug and allowing the passage of some food from time to time.

Figures 2A, 2B, 2C:
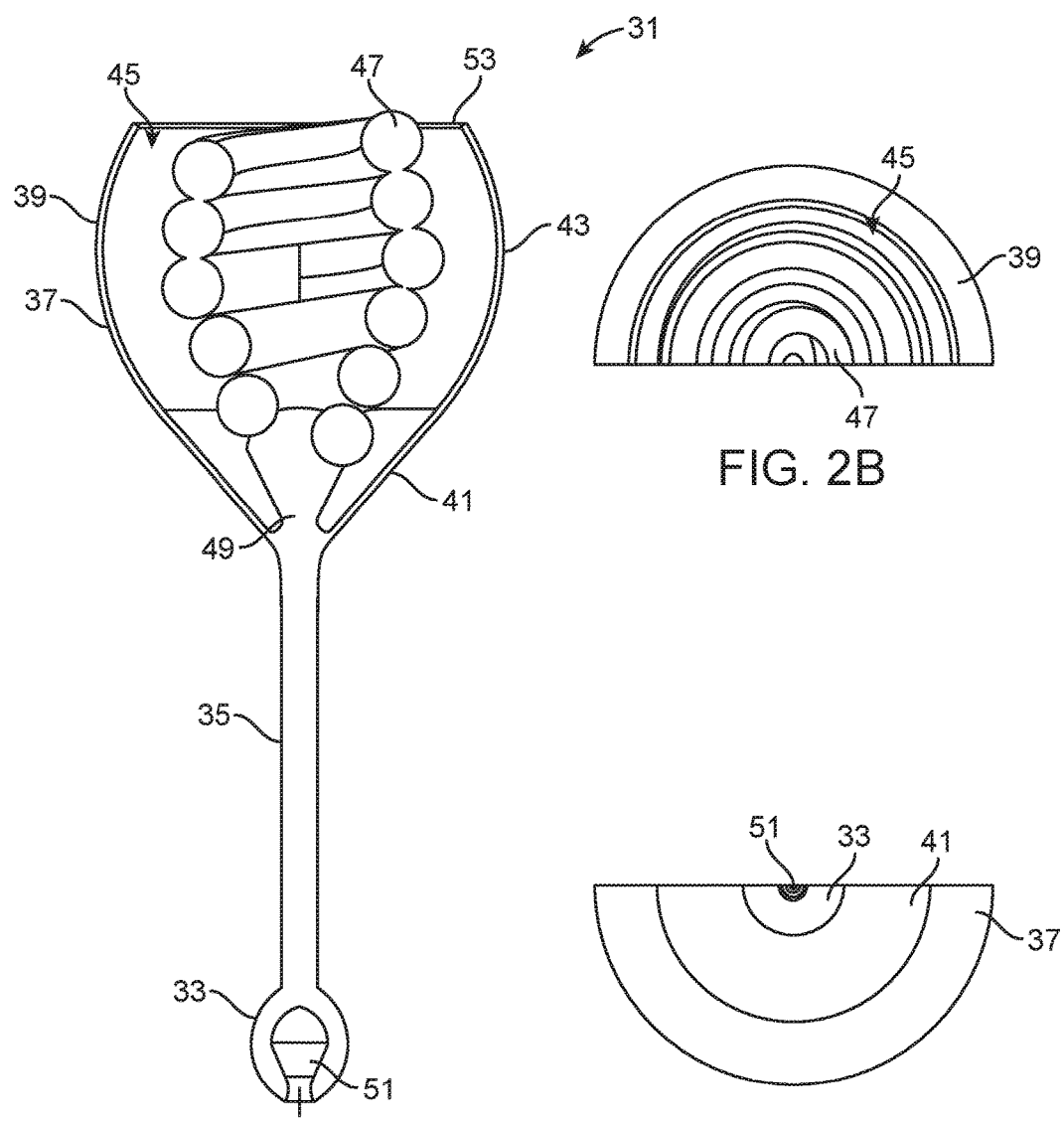
FIGS. 2A-2C illustrate respectively a cross-sectional side view and top and bottom end views of another embodiment.

Another embodiment is illustrated in the cross-sectional side view of FIG. 2A and the top and bottom end views, respectively, of FIGS. 2B and 2C. In this embodiment, device 31 may also include a distal member 33 connected or attached via tether 35 to proximal member 37. As described above, proximal member 37 may comprise an apron member 39 which defines a curved or otherwise arcuate surface which tapers radially from tether 35 at a distal portion 41 (which typically contacts the stomach interior surface when in use) to a curved proximal portion 43 which has a relatively larger diameter and which may define a circumferential lip or edge 53 which is atraumatic to surrounding tissue. Apron member 39 may define a channel or interstice 45 within which first occluding member 47 may reside when occluding member 47 is in its contracted deployment configuration, as illustrated. With occluding member 47 contracted, apron member 47 may be configured to entirely or at least partially encircle or enclose occluding member 47, as illustrated in FIGS. 2D and 2E which respectively show side and cross-sectional perspective views. Moreover, interstice 47 may be left open when in use in the patient body or an additional cap member or covering may be optionally attached to fully enclose apron member 39 and occluding member 47 within, if so desired.

Occluding member 47 may be formed into a coiled or wound structure having a plurality of turns and a distal end which is attached, coupled, or otherwise formed integrally with device 31 at connecting portion 49. Because of its coiled or wound helical structure, occluding member 47 may be extended in a low-profile configuration, as above, for delivery into the patient body and then allowed to compress or contract into its coiled structure which forms a diameter or cross-sectional area which is relatively larger than a diameter of distal member 33 to inhibit or prevent the passage of proximal member 37 through the pylorus when in use. As in the aforementioned embodiment, occluding member 47 may be biased or configured to self-contract. Alternatively, a string member or other locking mechanism, as described herein, may be actuated to compress and/or lock the structure such that the expanded configuration is maintained and prevented from releasing and reconfiguring back into its low-profile configuration. Distal member 33 may further define a lumen or channel 51 to facilitate the placement and/or positioning of device 31 within the patient body.

Figure 3A:
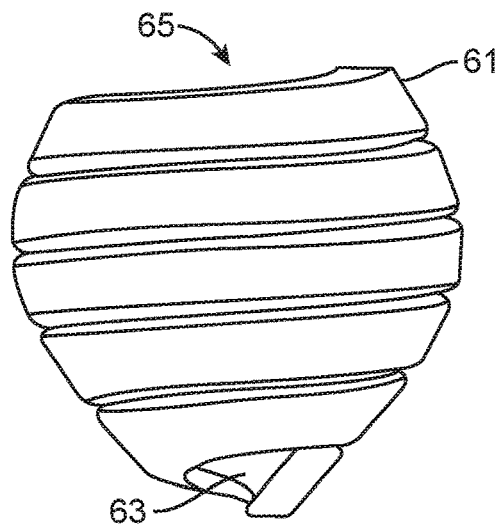
FIGS. 3A-3B illustrate side and cross-sectional side views, respectively, of yet another embodiment where an occluding member is separately fabricated and removably attachable within an apron member.
Figure 3B:
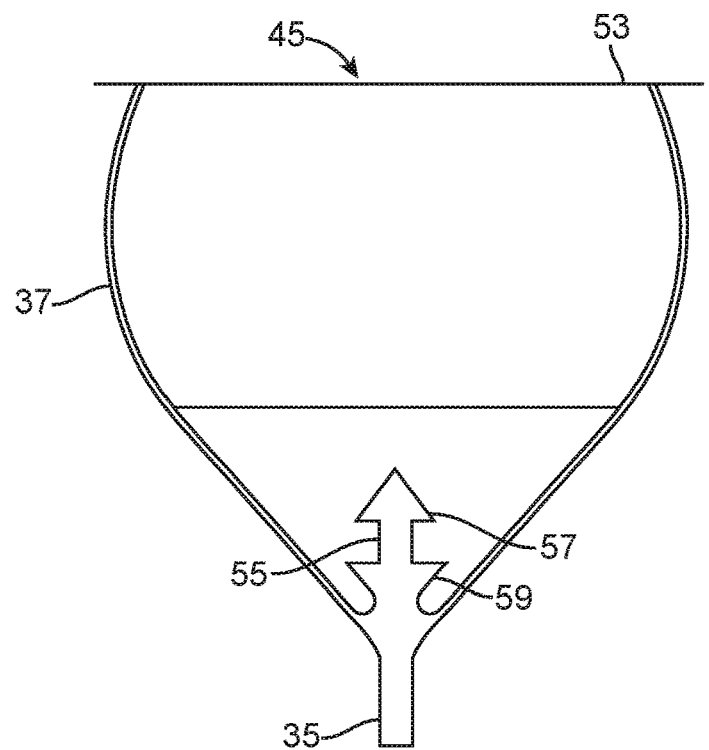

In yet another embodiment, the occluding member may be fabricated as a separate component and attached or coupled within the apron member at a later time rather than forming the occluding member as a continuous integral component. This particular embodiment allows for the size and shape of the occluding member to be varied and altered according to any patient-specific parameters and attached within a common apron member. As shown in the side view of FIG. 3A and the cross-sectional side view of FIG. 3B, occluding member 61 may be formed as a coiled or wound helical structure which defines a channel 65 and a receiving portion 63 when in its collapsed deployed configuration. As previously described, occluding member 61 may be advanced into the patient body in an extended low-profile configuration and then collapsed into its expanded and optionally locked configuration, as shown, either via actuation or by allowing for self-reconfiguration.

Because the coiled portion of occluding member 61 may form a receiving portion 63 in its collapsed configuration, portion 63 may be coupled to a complementary securement mechanism positioned within apron member 37. In this example, the securement mechanism may be comprised of a connecting portion 55 which extends distally within apron member 37. Connecting portion 55 may have a securement member 57, such as a tapered portion, and a stop member 59 which each limit the movement of portion 63 relative to connecting portion 55.

Figure 3C:
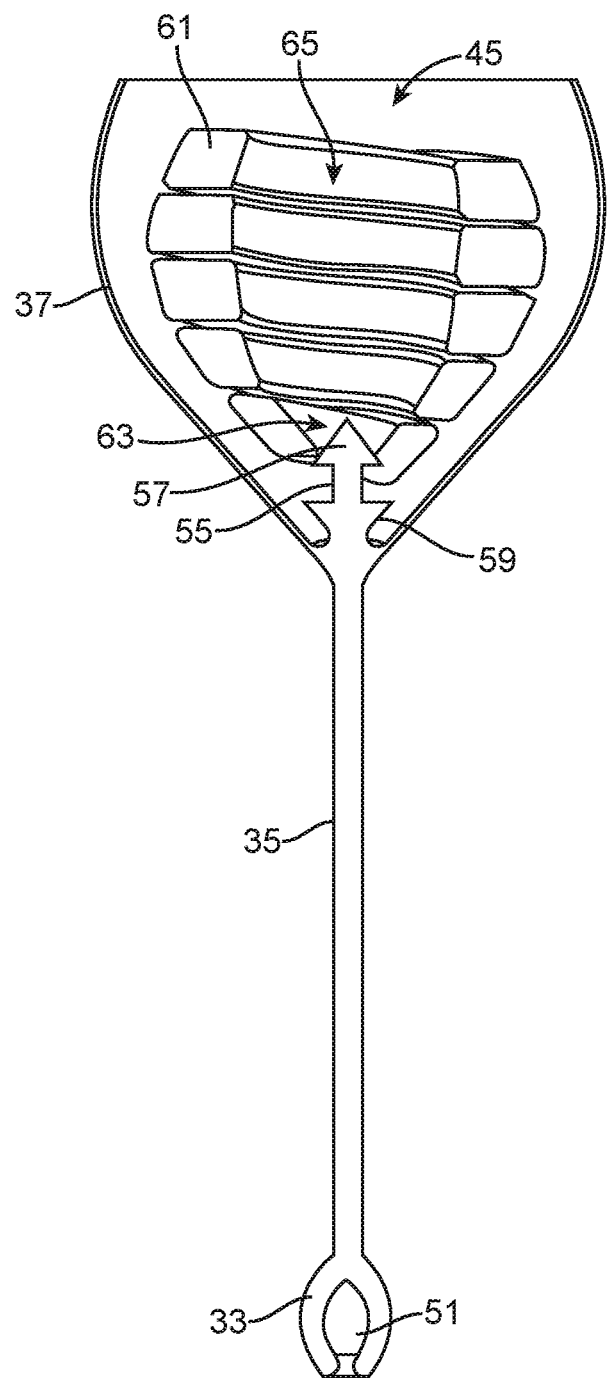
FIG. 3C illustrates a cross-sectional side view of an assembled device from FIGS. 3A and 3B.

As illustrated in the cross-sectional side view of FIG. 3C, occluding member 61 is shown in its collapsed and locked configuration while secured within interstice 45 and encircled by apron member 37. As shown, securement member 57 may be advanced at least partially within channel 65 formed by the wound occluding member 61 to prevent the relative movement or release of occluding member 61 from connecting portion 55. The connecting portion 55 is illustrated as an example and is not intended to be limiting. Other known securement mechanisms may be utilized as practicable.

In these and other embodiments described herein, because the device may be introduced into the patient body in a minimally invasive manner, e.g., per-orally and through the esophagus into the patient's stomach, the device may be delivered in its low-profile configuration, e.g., were the occluding member is in its uncoiled or unwound elongate configuration. Alternatively, the device may be delivered in a partially locked configuration. Once within the stomach, for instance, the device may be coiled or wound into its deployment configuration and the occluding member may be affirmatively locked into position relative to the device such that its enlarged profile inhibits or prevents the passage of the device through the pylorus. In ensuring that the occluding member is locked into its expanded configuration, various mechanisms may be utilized to confirm its securement.

One example includes having the string for locking the occluding member be color-coded such that one portion of the string is of a different color, e.g., red, than the remainder of the string. As the string is tensioned to lock the occluding member, once the color-coded portion is exposed from the device the user may visually confirm that the occluding member is locked into its deployment configuration. Alternatively, the amount of tension required to lock the device may be calibrated to increase to a preset level once the device is locked such that the user may confirm by tactile feedback that the device is indeed locked.

Other alternative mechanisms for locking confirmation or detection of the occluding device may additionally include sensors incorporated within the device. An example is illustrated in the cross-sectional side view of FIG. 1F, which shows sensor 67 positioned within the device. Sensor 67 may incorporate any number of detection modalities, e.g., acoustic, ultrasonic, electrical, electromagnetic, optical (for instance, detecting changes in color, wavelength, frequency, etc.), chemical, etc. which may sense changes in the occluding member from its coiled deployment configuration or changes in the string tension, connecting member 56, or release member 58.

Based on the foregoing, device 30 (and variations thereof) assists in the treatment of obesity by limiting the passage of food from the stomach into the intestine, and at the same time by reducing the intake of food by the patient due to the sense of fullness generated by the retention of food in the stomach for a longer time and also by to the presence of device 30 in the stomach.

In yet another variation of the helically coiled device, FIGS. 4A and 4B show perspective views of a helical assembly 70 having a proximal member 72 reconfigured from its elongated configuration into its enlarged, coiled and nested configuration. The tether 74 may be seen extending from a compliant region 78 near a distal end of the proximal member 72 and a distal member 76 attached at a distal end of the tether 74. The compliant region 78 may be provided with a variable stiffness to be more benign to the contacted tissue and to further prevent trauma to the surrounding tissue. In this and any of the variations herein, various coatings may be applied to the device, for example, for coefficient of friction, lubricity, enhanced biochemical durability, anti-microbial performance, etc.

FIG. 4B shows a cross-sectional side view of the coiled and locked assembly 70 which in this variation illustrates the elongate coiled member 80 having a contoured profile 84. The profile 84 may define a projecting portion which may form a contact interface 82 when coiled into its nesting configuration with the adjacent coil although reversed contours may also be used to prevent the inward displacement of the nested loops. The contoured profile 84 may also enhance alignment of the structure during deployment as well. Furthermore, the edges of the coiled member 80 may also be radiused to reduce exposure of any edges to the gastric tissue. Once nested, the coiled member 80 may form a compacted shape which may form an enclosed space 88 within and which may be configured into a spherically-shaped structure, as shown. To maintain its compacted configuration, a central column 86 may extend through the center of the proximal member 72 to lock the shape of the member 72. The central column 86 may be formed in part by a distal hub 90 which may be anchored or attached at a distal end of the proximal member 72 and also optionally attached to the hub where the tether 74 is attached to the proximal member 72. A proximal plug 94 may be seated 96 at a proximal end of the coiled member 80 and extend into an coupled attachment to the distal hub 90 which may be connected via, e.g., a collar 92 such as a directional C-clip, etc.

Optionally, a reinforcing member 98 such as a wire or suture length may be coupled to the distal hub 90 and extend through the tether 74 into attachment with the distal member 76. Additionally, a distal weight 100 may also be optionally integrated in the distal member 76 as well. The inclusion of a reinforcing member 98 may prevent the over-extension of the tether 74 during deployment and use. The member 98 may also function to prevent the detachment of the tether 74 or distal member 76 in the unlikely event that the tether 74 fails.

Figure 5A:
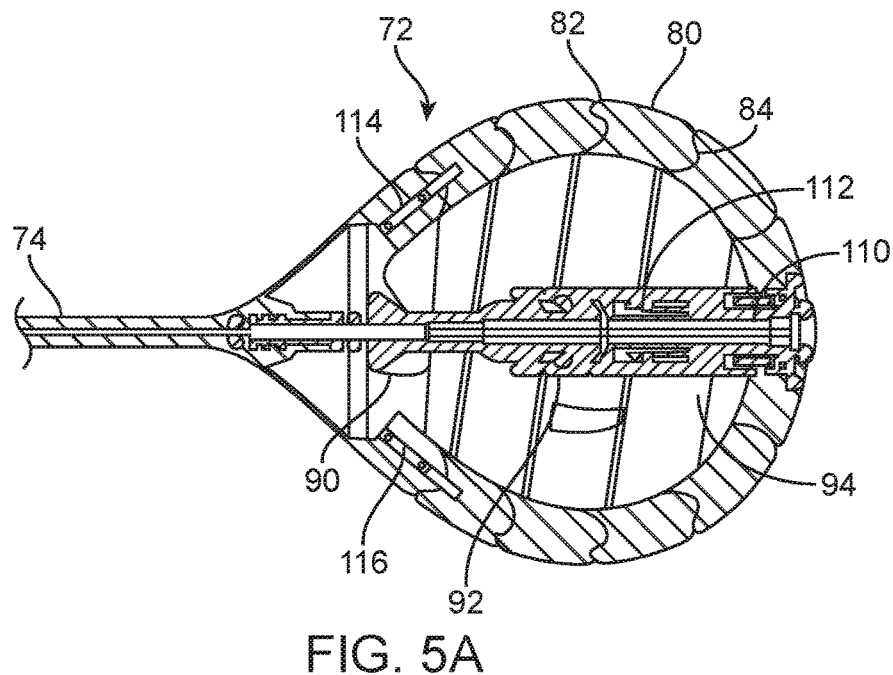
FIGS. 5A and 5B show cross-sectional side and perspective views of the proximal member to illustrate detail features for locking the proximal member into its enlarged and compacted configuration.
Figure 5B:
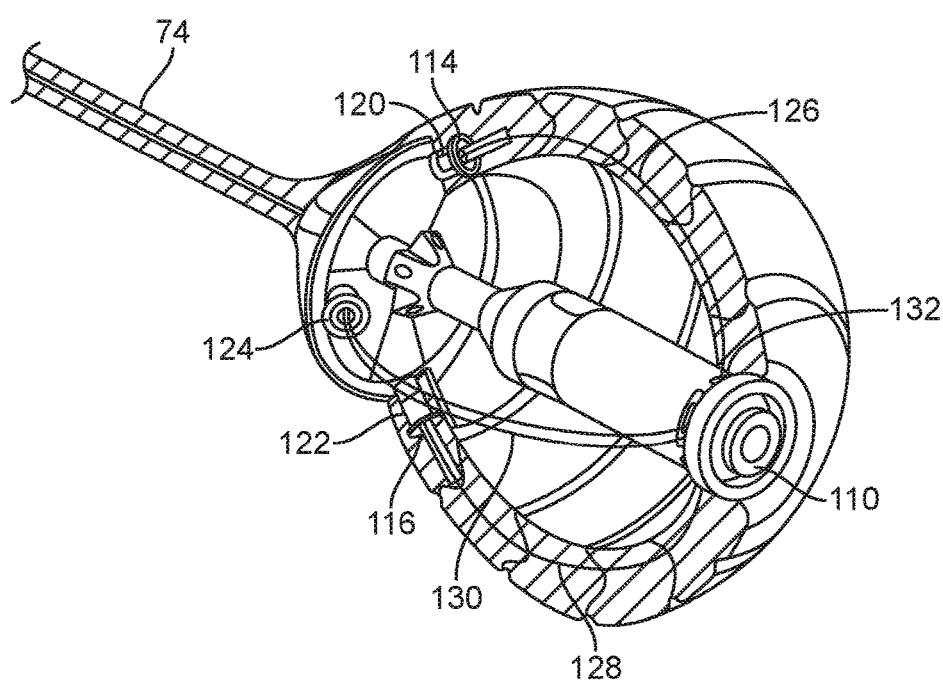

FIGS. 5A and 5B show cross-sectional side and perspective views of the proximal member 72 to illustrate detail features for locking the proximal member 72 into its enlarged and compacted configuration. As shown, the proximal plug 94 may include a release mechanism 110 which extends through a proximal end of the plug 94 and is secured via one or more release securement members 112 within the plug 94. The release mechanism 110 may be toggled proximally and distally relative to the plug 94 to selectively lock or unlock one or more tensioning wires which extend transversely through the coiled member 80. Moreover, the release mechanism 110 may be formed to have a rigid lip to facilitate its grasping by endoscopic tools when locking or unlocking the mechanism 110. Optionally, the release mechanism 110 may also integrated a valve, such as a duck-billed valve, to prevent solid matter from entering the internal space of the proximal member 72. The collar 92 may also be seen coupling the distal hub 90 and the proximal plug 94 to one another. As the coiled member 80 configures into the enlarged configuration, the plug 94 may come into it mating engagement with the distal hub 90 which may then be joined by the collar 92 housed around the proximal plug 94.

To facilitate the reconfiguration of the coiled member 80 into its compacted configuration and to lock its enlarged configuration in a secure manner, one or more tensioning wires may extend through the coiled member 80 in a transverse direction. The tensioning wires may be formed of various wires or other high-strength force fibers. The terminal end of the coiled member 80 may integrate one or more tensioning wire pins 114, 116, as shown in FIG. 5A, to which one or more corresponding collets 120, 122, 124 are attached and which also have corresponding lock lines 126, 128, 130 extending from their respective pins. The lock lines 126, 128, 130 may be located uniformly about the circumference of the proximal member and extend transversely through respective lumens defined through the coiled member 80, as shown in FIG. 5B. Although three lock lines are shown, this is done for illustrative purposes and any number of lock lines may be utilized at uniform (e.g., four lock lines positioned at 90 degrees relative to one another about a circumference of the proximal member 72) or arbitrary locations around the proximal member 72. Moreover, multiple lock lines may further provide for locking redundancy such that if one lock line were to fail, the proximal member 72 may still retain its enlarged structure.

With the lock lines extending through the coiled member, they may pass and loop through corresponding openings 132 located near or at the proximal end of the proximal plug 94. The remaining terminal ends of each of the lock lines may be passed externally of the assembly 70 as well as externally of the patient body when in use to facilitate the tensioning and securement of the lock lines when collapsing the proximal member 72. With the looped lock lines passing through opening 132, the release mechanism 110 may be selectively collapsed into the proximal plug 94 to lock the tensioning in the lock lines which may maintain the compacted configuration of the proximal member 72. Pulling of the release mechanism 110 may accordingly release the lock lines and allow for the unraveling of the proximal member 72, e.g., during removal of the device from the patient's stomach.

To facilitate the tensioning of the lock lines, they may be engaged through the respective collets to allow for unidirectional passage of the lock lines. Thus, as the lock lines are tensioned through the collets, they may be pulled in only a tensioning direction to prevent or inhibit the unraveling of the proximal member 72. Additionally, the collets or pins may be optionally radio-opaque to facilitate visualization of the device through, e.g., fluoroscopic visualization, to provide for confirmation of the locked status of the proximal member 72.

In yet another variation. FIGS. 6A and 6B show perspective and cross-sectional perspective views of a covered obstructing assembly 140. In this variation, a covering 142 may enclose the coiled member 80 partially or completely such that the surface presented to the surrounding tissue remains completely smooth and uniform. The covering 142 may approximate the enlarged shape of the proximal member 72 such that the coiled member 80 may be formed entirely within the covering 142 itself, as described herein. Once the coiled member 80 has been formed within, a tissue interface 144 may be positioned by the terminal end of the coiled member 80 so as to present a smooth surface against the surrounding tissue.

As shown in the cross-sectional perspective view of FIG. 6B, a strain relief hub section 146 may be incorporated between the covering 142 and tether 74 so as to prevent the excessive strain at the connection point due to the softened structure. The strain relief hub section 146 may be internally expandable such that it is rotationally secure. It may also be provided as a single-molded pan that can be expanded by compression. An attachment collar 148, in an alternative variation, may extend into the receiving space 152 defined within the covering 142 and the proximal plug 94 may be detached from the distal hub 90 such that the central column is discontinuous. The attachment collar 148 may be configured to receive the pins at the terminal ends of the lock lines to lock the proximal member 72 in its configuration and may also join the member 72 to the covering 142. Having a decoupled column may provide for additional flexibility to the proximal member 72 which may conform or flex to a greater extent. With the covering 142 deployed first, the coiled member 80 may be introduced in its elongate configuration directly through cover opening 150 and into the receiving space 152 where it may coil into its nested and collapsed configuration, as described herein.

Figure 7:
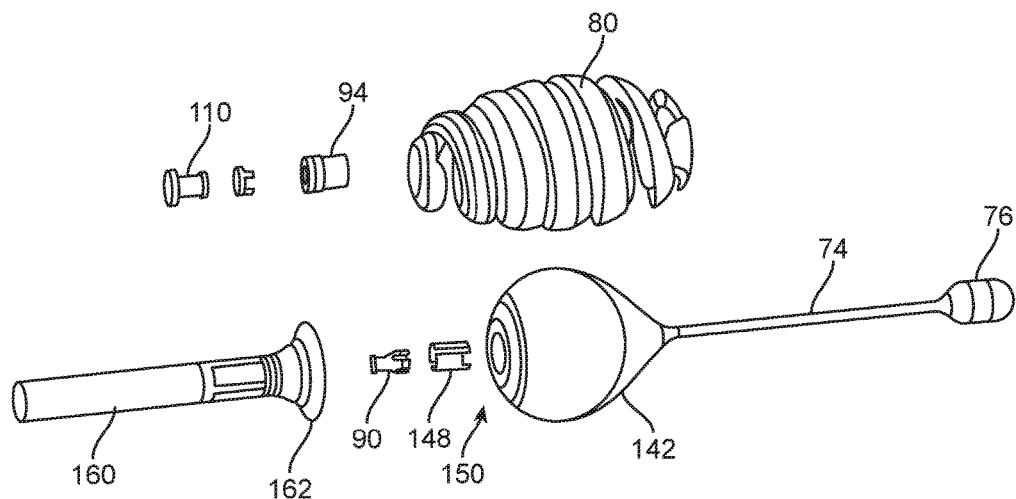
FIG. 7 shows a perspective assembly view of the various components which may form the covered embodiment.
Figure 8:
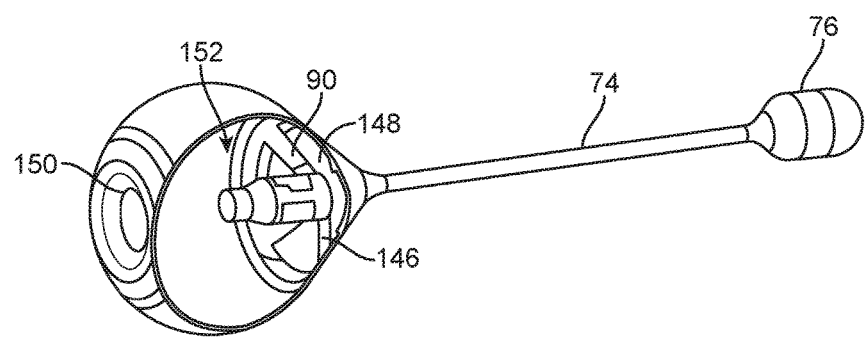
FIG. 8 shows a partial cross-sectional perspective view of the covering having a distal hub and attachment collar within the receiving, space.

FIG. 7 shows a perspective assembly view of the various components which may form the covered embodiment. As shown, the covering 142 may incorporate the distal hub 90 and attachment collar 148 within the receiving space 152, as shown in the partial cross-section perspective view of FIG. 8. The coiled member 80 may be introduced into the receiving space 152 through opening 150 as a component separate from the covering 142. As previously described, the proximal plug 94 and release mechanism 110 may also be integrated with the coiled member 80. Additionally, a delivery tube 160 having a tapered covering interface 162 may be provided for attachment to the opening 150. The delivery tube 160 may provide an access passage for the introduction of the coiled member 80 in its elongate form into the covering 142.

Figure 9A:
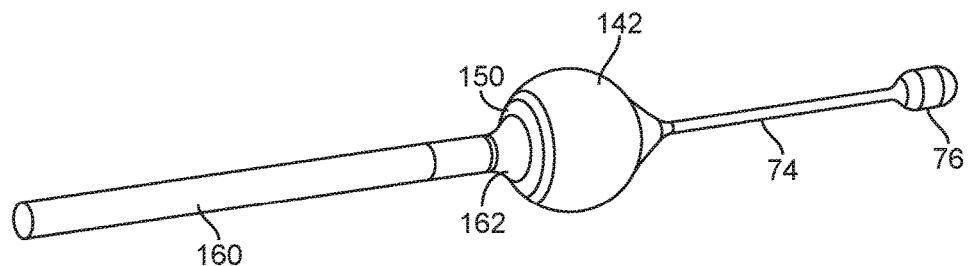
FIGS. 9A-9C illustrate partial cross-sectional perspective views of an example showing how the coiled member may be deployed within the covering.
Figure 9B:
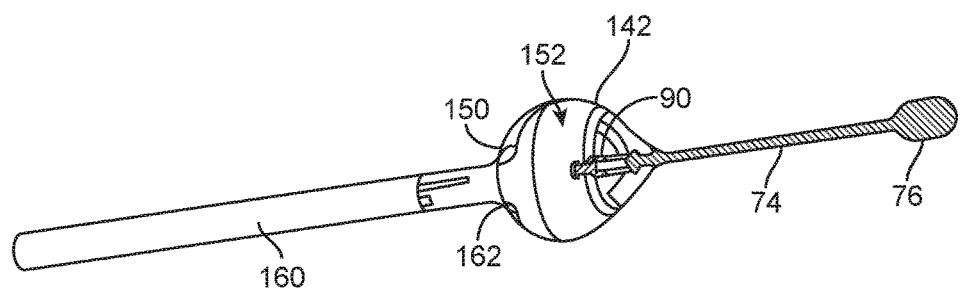
Figure 9C:
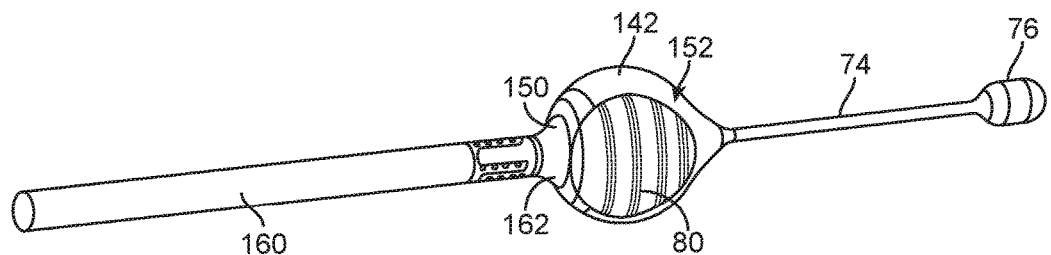

FIGS. 9A to 9C illustrate partial cross-sectional perspective views of an example showing how the coiled member 80 may be deployed. With the covering 142 attached temporarily to the covering interface 162 at opening 150, as shown in FIG. 9A, the covering 142 may be positioned within the stomach. FIG. 9B illustrates how the covering 142 may be devoid of the coiled member 80. As shown in FIG. 9C, the coiled member 80 may then be introduced through the delivery tube 160 and into the receiving space 152 where it may then coil into its nested and compacted configuration. Once complete, the covering interface 162 may be pulled from the opening 150 to detach itself and the tissue interface 144 and release mechanism 110 may obstruct or plug the covering opening 150.

Figure 10:
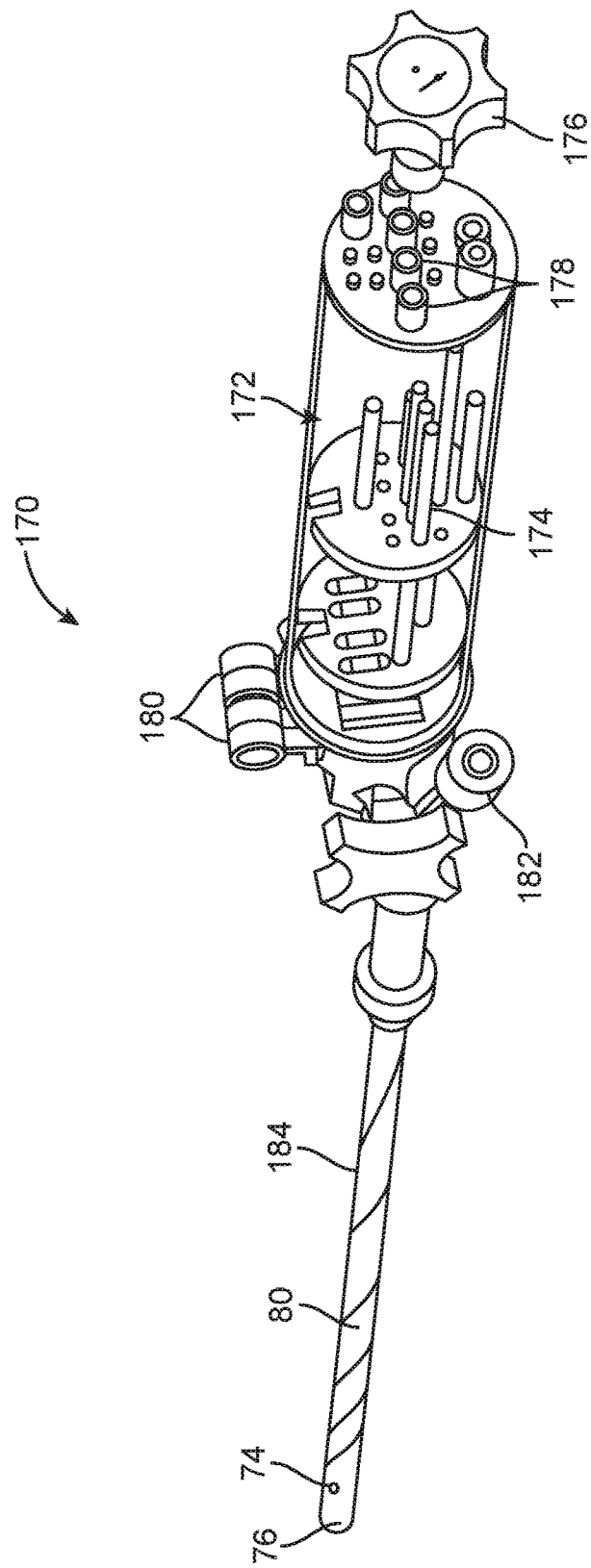
FIG. 10 shows one variation of a delivery assembly.

In delivering and deploying the obstructing device into the stomach, one variation of a delivery assembly 170 is shown in the perspective view of FIG. 10. In this example, the assembly 170 may generally having a tensioning control assembly 172 attached to a delivery tube 184 extending, from the control assembly 172. The coiled member 80 may be loaded within the delivery tube 184 in its elongated configuration with the tether 74 and distal member 76 positioned within the delivery tube 184 distal to the coiled member 80. The lock lines may pass from the elongate member 80 within the delivery tube 184 and extend proximally through the delivery tube 184 and into the control assembly 172. Each of the lock lines may be routed to a corresponding tensioning spring 174 which may provide a continual or intermittent tensioning force of variable magnitude upon the lock lines which may help to prevent the lock lines from tangling and which may also facilitate the tensioning of the lock lines when reconfiguring the coiled member 80 into its compacted shape.

Each of the lock lines may also be attached to a corresponding tension control interface 178 which may tighten each of the lock lines individually or simultaneously, e.g., via an actuatable loop tensioner 176. Each of the lock lines may be further routed through the control assembly 172 and into communication with a corresponding tensioning, wire access handle 180. Once the proximal member 72 has been sufficiently nested and compacted, one or more of the wire access handles 180 may be pulled to expose the lock lines which may then be cut and/or removed from the assembly and patient. An optional insufflation port. 182 coupled to the delivery tube 184 may also be provided, e.g., for insufflating the stomach or body lumen prior to or during delivery of the obstructing member.

Figure 11A:
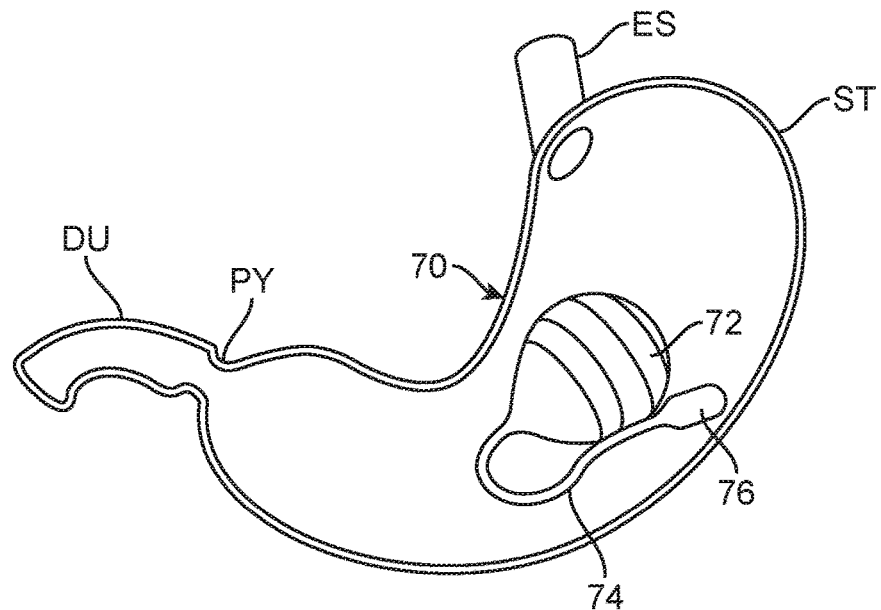
FIGS. 11A and 11B show partial cross-sectional views of the device placed within the stomach.
Figure 11B:
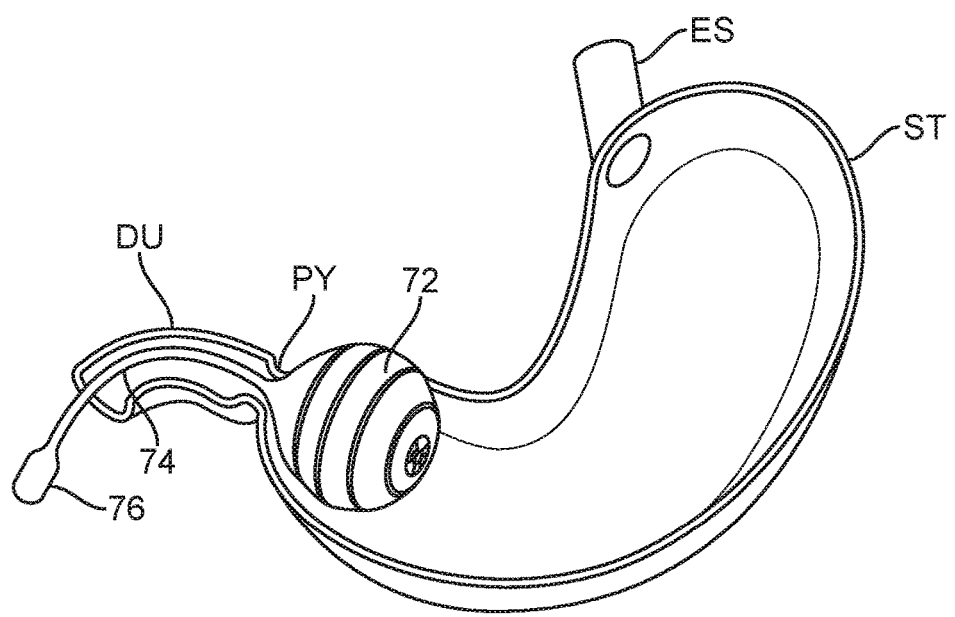

When deployed, the obstructing device 70 may be placed within the stomach ST of a patient, as shown in the partial cross-sectional view of FIG. 11A. The esophagus ES, pylorus PY, and duodenum DU are also illustrated for reference. With the proximal member 72 in its enlarged and nested configuration, the device 70 may lie within the stomach ST. Once the patient has ingested some food or liquid, the stomach ST may begin to contract such that the distal member 76 is moved through the stomach ST towards the pylorus PY. Because the distal member 76 is sized for passage through the pylorus PY, the distal member 76 may pass through to become positioned within the duodenum DU of the patient. However, because of the enlarged configuration, the proximal member 72 may remain within the stomach ST and cover the pylorus PY, as shown in FIG. 11B. As the stomach continues to contract, the proximal member 72 may begin to intermittently obstruct and expose the pylorus PY allowing food and/or liquid to pass from the stomach at a slowed rate thus forcing the patient to feel full for longer periods of time. Once the stomach has been completely emptied, the device 70 may be allowed to then reposition itself within the stomach ST.

Figure 12A:
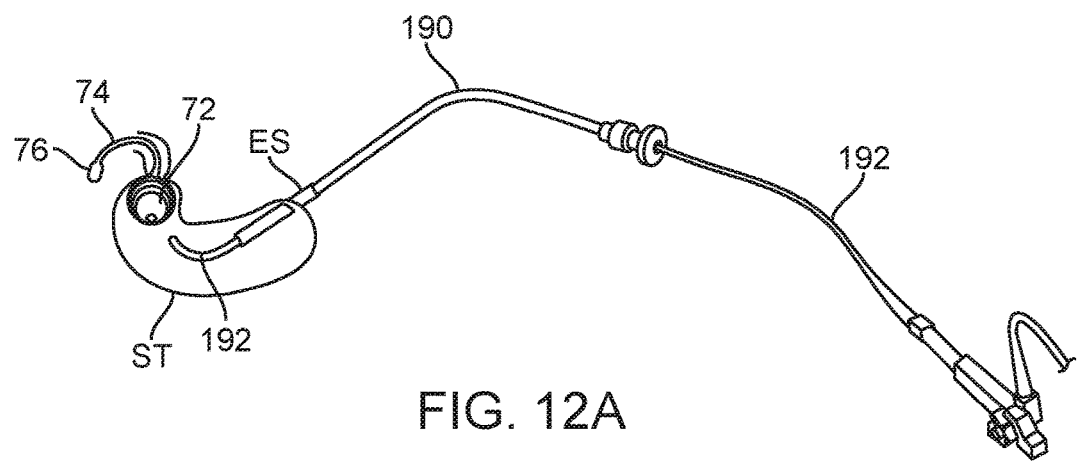
FIG. 12A shows a perspective view of an optional access tube positioned through the esophagus for removal of the device from a patient.
Figure 12B:
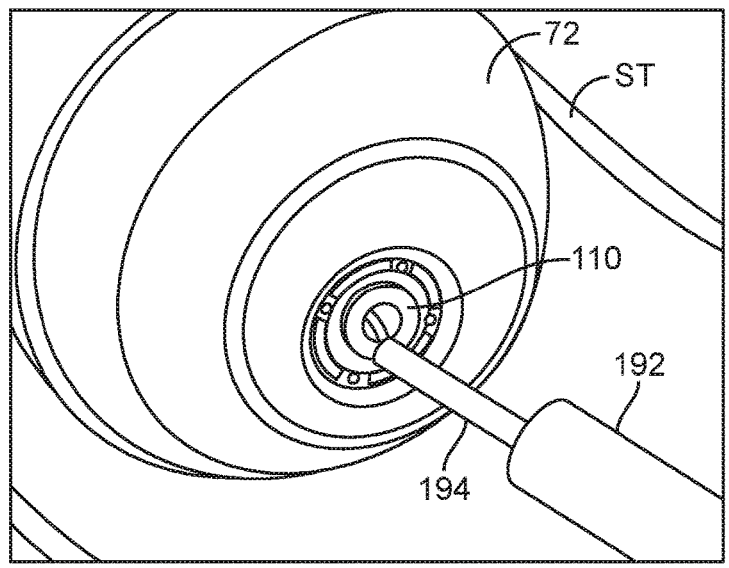
FIG. 12B shows a perspective view of a grasper brought into contact with a release mechanism.
Figure 12C:
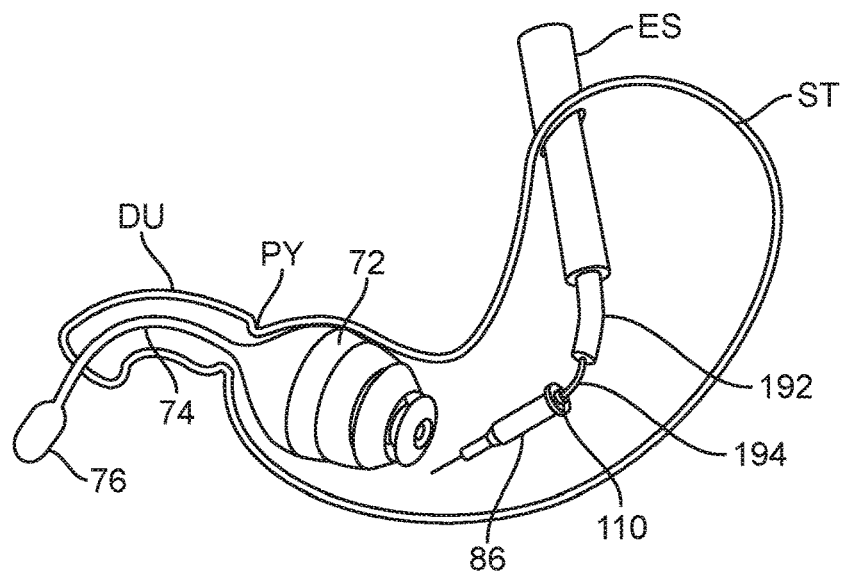
FIGS. 12C and 12D show an example of the proximal member being unlocked and removed from a stomach in its elongate configuration.
Figure 12D:
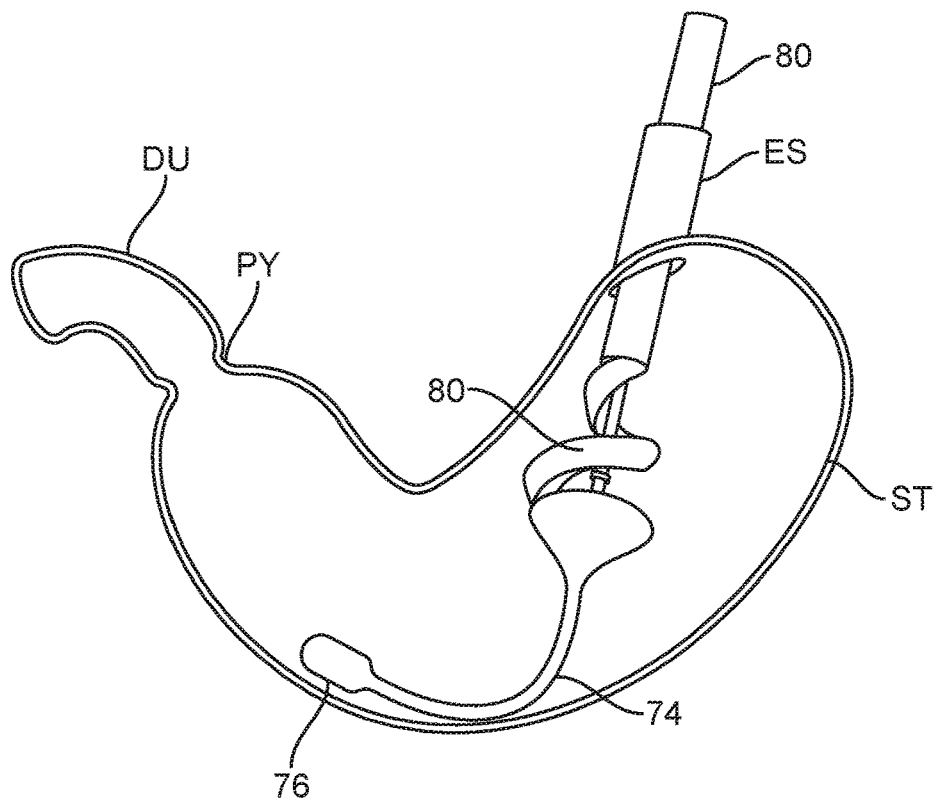

In the event that the device 70 is to be removed from the patient, the device 70 may be collapsed within the stomach ST and removed back through the esophagus ES in its elongate configuration. One example is shown in the perspective view of FIG. 12A which illustrates how an optional access tube 190 may be positioned through the esophagus ES and an endoscope 192 or other instrument having, e.g., a grasper 194, may be passed through the access tube 190 and into proximity to the proximal member 72. The grasper 194 may be brought into contact with the release mechanism 110, as shown in the perspective view of FIG. 12B, which may then be pulled to unlock the proximal member 72. The entire central column 86 may be removed from the proximal member 72, as shown in FIG. 12C, and removed from the stomach ST. With the proximal member 72 released, the coiled member 80 may be pulled through the access tube 190 and through the esophagus ES in its collapsed and elongate profile, as shown in FIG. 12D.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill, in the arts are intended to be within the scope of this disclosure. Moreover, various combinations of aspects between examples are also contemplated and are considered to be within the scope of this disclosure as well.

What is claimed is:

1. A device for intermittently obstructing a gastric opening, the device comprising:
  a proximal occluding member, wherein the proximal occluding member is reconfigurable between an elongated, narrowed configuration and a compacted, widened configuration having a plurality of turns nesting one adjacent to the other;
  a distal member having a size which is smaller than the compacted, widened configuration of the proximal occluding member;
  a flexible tether connecting the proximal occluding member and the distal member;
  a locking mechanism positioned within the proximal occluding member, wherein the locking mechanism is positionable between a locked state where the compacted, widened configuration is maintained and an unlocked state where the proximal occluding member becomes elongated; and
  a plurality of lock lines extending transversely through the plurality of turns of the proximal occluding member and coupling a distal end of the proximal occluding member with a proximal end of the proximal occluding member, wherein the lock lines are arranged uniformly around a circumference of the proximal occluding member.

2. The device of claim 1, wherein the lock lines extend transversely through the proximal occluding member in a curvilinear manner through lumens defined through the plurality of turns of the proximal occluding member.

3. The device of claim 1 wherein the locking mechanism further comprises a distal hub coupled to a distal end of the proximal occluding member and a proximal plug coupled to a proximal end of the proximal occluding member.

4. The device of claim 3 wherein the distal hub and proximal plug are configured to engagingly mate with one another.

5. The device of claim 3 wherein the distal hub and proximal plug are detached and maintained at a distance from one another when the proximal occluding member is in the compacted, widened configuration.

6. The device of claim 1 further comprising a covering attached to the flexible tether and surrounding the proximal occluding member.

7. The device of claim 6 further comprising a delivery tube which is removably coupled to an opening defined along a proximal end of the covering wherein the delivery tube is configured to provide access passage for the introduction of the proximal occluding member having the plurality of turns into the covering.

8. The device of claim 1 wherein the distal member further comprises a weight disposed within the distal member.

9. The device of claim 1, wherein the proximal occluding member further comprises one or more tensioning wire pins or collets configured to apply tension to the lock lines.

10. The device of claim 1, wherein edges of the plurality of turns are radiused to reduce trauma to gastric tissue.

11. A method of deploying an occluding device within a patient, comprising:
  advancing an obstructing device into a stomach of the patient, the obstructing device having a proximal occluding member configured in an elongated, narrowed configuration and having a distal member and a flexible tether connecting the proximal occluding member and the distal member;
  urging the proximal occluding member into a compacted, widened configuration having a plurality of turns nesting one adjacent to the other by tensioning a plurality of lock lines extending transversely through the plurality of turns of the proximal occluding member, wherein the lock lines are arranged uniformly around a circumference of the proximal occluding member;
  positioning a distal hub connected to a distal end of the proximal occluding member and a proximal plug connected to a proximal end of the proximal occluding member into proximity to one another; and
  locking a position of the distal hub and the proximal plug relative to one another such that the compacted, widened configuration is maintained.

12. The method of claim 11 wherein advancing an obstructing device comprises introducing the obstructing device through an esophagus and into the stomach.

13. The method of claim 11 wherein urging the proximal occluding member comprises compacting the proximal occluding member into a helical structure where the plurality of turns nest in an interfitted profile.

14. The method of claim 11 wherein urging the proximal occluding member comprises tensioning the lock lines extending transversely through one or more lumens defined along the plurality of turns of the proximal occluding member by pulling the one or more lock lines through collets.

15. The method of claim 11 wherein urging the proximal occluding member into the compacted, widened configuration comprises introducing the proximal occluding member through an opening defined along a covering.

16. The method of claim 11 wherein positioning the distal hub comprises engaging the distal hub and proximal plug to one another.

17. The method of claim 11 wherein positioning the distal hub comprises maintaining the distal hub and proximal plug at a distance from one another when the proximal occluding member is in the compacted, widened configuration.

18. The method of claim 11 wherein locking a position comprises engaging a locking mechanism along the proximal plug such that one or more locking lines through the proximal occluding member are secured.

19. The method of claim 11 further comprising disabling a locking mechanism along the proximal occluding member such that the proximal occluding member reconfigures into an elongated, narrowed configuration.

20. The method of claim 19 further comprising withdrawing the proximal occluding member from the stomach of the patient.

* * * * *